(12) United States Patent
Shelton, IV et al.

(10) Patent No.: US 8,322,455 B2
(45) Date of Patent: Dec. 4, 2012

(54) MANUALLY DRIVEN SURGICAL CUTTING AND FASTENING INSTRUMENT

(75) Inventors: Frederick E. Shelton, IV, New Vienna, OH (US); John N. Ouwerkerk, Cincinnati, OH (US); Jerome R. Morgan, Cincinnati, OH (US); Jeffrey S. Swayze, Hamilton, OH (US); Eugene L. Timperman, Cincinnati, OH (US); Leslie M. Fugikawa, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1207 days.

(21) Appl. No.: 11/475,412

(22) Filed: Jun. 27, 2006

(65) Prior Publication Data
US 2007/0295780 A1 Dec. 27, 2007

(51) Int. Cl.
*E21B 37/06* (2006.01)
(52) U.S. Cl. .................. 173/1; 227/19; 227/180.1
(58) Field of Classification Search .......... 227/19, 227/176.1, 180.1; 74/851, 841; 192/21
See application file for complete search history.

(56) References Cited

U.S. PATENT DOCUMENTS

| 2,037,727 A | 4/1936 | Chapelle |
| 2,853,074 A | 9/1958 | Olson |
| 2,959,974 A * | 11/1960 | Emrick et al. .......... 74/379 |
| 3,490,675 A | 1/1970 | Green at al. |
| 3,551,987 A | 1/1971 | Wilkinson |
| 3,643,851 A | 2/1972 | Green et al. |
| 3,662,939 A | 5/1972 | Bryan |
| 3,717,294 A | 2/1973 | Green |
| 3,819,100 A * | 6/1974 | Noiles et al. .......... 227/19 |
| 3,894,174 A | 7/1975 | Cartun |
| 3,940,844 A | 3/1976 | Colby et al. |
| 4,331,277 A | 5/1982 | Green |
| 4,383,634 A | 5/1983 | Green |
| 4,396,139 A | 8/1983 | Hall et al. |
| 4,402,445 A | 9/1983 | Green |
| 4,415,112 A | 11/1983 | Green |
| 4,429,695 A | 2/1984 | Green |

(Continued)

FOREIGN PATENT DOCUMENTS

CA 2458946 A1 3/2003

(Continued)

OTHER PUBLICATIONS

C.C. Thompson et al., "Peroral Endoscopic Reduction of Dilated Gastrojejunal Anastomosis After Roux-en-Y Gastric Bypass: A Possible New Option for Patients with Weight Regain," Surg Endosc (2006) vol. 20, pp. 1744-1748.

(Continued)

*Primary Examiner* — Rinaldi Rada
*Assistant Examiner* — Nathaniel Chukwurah

(57) ABSTRACT

A surgical cutting and fastening instrument that includes an elongate channel that is attached to a handle assembly by an elongate shaft assembly. The elongate channel is configured to receive a cartridge and has a pivotally translatable anvil attached thereto and a knife bar supported therein. The anvil may be selectively opened and closed by manipulating a closure trigger supported by the handle assembly. The knife bar may be distally advanced through the elongate channel by actuating a firing trigger that cooperates with a reversible rotary drive supported by the handle assembly. The knife bar may also be retracted to its starting position by actuating the firing trigger after the reversible rotary drive has been shifted to a retraction orientation.

23 Claims, 18 Drawing Sheets

U.S. PATENT DOCUMENTS

| | | | |
|---|---|---|---|
| 4,475,679 A | 10/1984 | Fleury, Jr. | |
| 4,489,875 A | 12/1984 | Crawford et al. | |
| 4,500,024 A | 2/1985 | DiGiovanni et al. | |
| 4,505,273 A | 3/1985 | Braun et al. | |
| 4,505,414 A | 3/1985 | Filipi | |
| 4,506,671 A | 3/1985 | Green | |
| 4,520,817 A | 6/1985 | Green | |
| 4,522,327 A | 6/1985 | Korthoff et al. | |
| 4,526,174 A | 7/1985 | Froehlich | |
| 4,530,453 A | 7/1985 | Green | |
| 4,565,109 A * | 1/1986 | Tsay | 475/305 |
| 4,566,620 A | 1/1986 | Green et al. | |
| 4,573,622 A | 3/1986 | Green et al. | |
| 4,580,712 A | 4/1986 | Green | |
| 4,606,343 A | 8/1986 | Conta et al. | |
| 4,610,383 A | 9/1986 | Rothfuss et al. | |
| 4,619,262 A | 10/1986 | Taylor | |
| 4,629,107 A | 12/1986 | Fedotov et al. | |
| 4,632,290 A | 12/1986 | Green et al. | |
| 4,655,222 A | 4/1987 | Florez et al. | |
| 4,664,305 A | 5/1987 | Blake, III et al. | |
| 4,671,445 A | 6/1987 | Barker et al. | |
| 4,709,120 A | 11/1987 | Pearson | |
| 4,715,520 A | 12/1987 | Roehr, Jr. et al. | |
| 4,728,020 A | 3/1988 | Green et al. | |
| 4,752,024 A | 6/1988 | Green et al. | |
| 4,754,909 A | 7/1988 | Barker et al. | |
| 4,767,044 A | 8/1988 | Green | |
| 4,805,823 A | 2/1989 | Rothfuss | |
| 4,809,695 A | 3/1989 | Gwathmey et al. | |
| 4,817,847 A | 4/1989 | Redtenbacher et al. | |
| 4,819,853 A | 4/1989 | Green | |
| 4,821,939 A | 4/1989 | Green | |
| 4,844,068 A | 7/1989 | Arata et al. | |
| 4,869,414 A | 9/1989 | Green et al. | |
| 4,869,415 A | 9/1989 | Fox | |
| 4,880,015 A | 11/1989 | Nierman | |
| 4,892,244 A | 1/1990 | Fox et al. | |
| 4,941,623 A | 7/1990 | Pruitt | |
| 4,944,443 A | 7/1990 | Oddsen et al. | |
| 4,955,959 A | 9/1990 | Tompkins et al. | |
| 4,973,274 A * | 11/1990 | Hirukawa | 440/1 |
| 5,027,834 A | 7/1991 | Pruitt | |
| 5,031,814 A | 7/1991 | Tompkins et al. | |
| 5,040,715 A | 8/1991 | Green et al. | |
| 5,065,929 A | 11/1991 | Schulze et al. | |
| 5,071,430 A | 12/1991 | de Salis et al. | |
| 5,080,556 A | 1/1992 | Carreno | |
| 5,106,008 A | 4/1992 | Tompkins et al. | |
| 5,111,987 A | 5/1992 | Moeinzadeh et al. | |
| 5,129,570 A | 7/1992 | Schulze et al. | |
| 5,137,198 A | 8/1992 | Nobis et al. | |
| 5,139,513 A | 8/1992 | Segato | |
| 5,156,315 A | 10/1992 | Green et al. | |
| 5,158,567 A | 10/1992 | Green | |
| 5,209,747 A | 5/1993 | Knoepfler | |
| 5,211,649 A | 5/1993 | Kohler et al. | |
| 5,221,036 A | 6/1993 | Takase | |
| 5,222,975 A | 6/1993 | Crainich | |
| 5,236,440 A | 8/1993 | Hlavacek | |
| 5,246,156 A | 9/1993 | Rothfuss et al. | |
| 5,253,793 A | 10/1993 | Green et al. | |
| 5,258,009 A | 11/1993 | Conners | |
| 5,271,543 A | 12/1993 | Grant et al. | |
| RE34,519 E | 1/1994 | Fox et al. | |
| 5,275,323 A | 1/1994 | Schulze et al. | |
| 5,282,806 A | 2/1994 | Haber et al. | |
| 5,282,829 A | 2/1994 | Hermes | |
| 5,304,204 A | 4/1994 | Bregen | |
| 5,307,976 A | 5/1994 | Olson et al. | |
| 5,312,024 A | 5/1994 | Grant et al. | |
| 5,318,221 A | 6/1994 | Green et al. | |
| 5,342,395 A | 8/1994 | Jarrett et al. | |
| 5,342,396 A | 8/1994 | Cook | |
| 5,350,400 A | 9/1994 | Esposito et al. | |
| 5,366,479 A | 11/1994 | McGarry et al. | |
| 5,379,933 A | 1/1995 | Green et al. | |
| 5,383,880 A | 1/1995 | Hooven | |
| 5,383,888 A | 1/1995 | Zvenyatsky et al. | |
| 5,395,033 A | 3/1995 | Byrne et al. | |
| 5,397,046 A | 3/1995 | Savage et al. | |
| 5,397,324 A | 3/1995 | Carroll et al. | |
| 5,403,312 A | 4/1995 | Yates et al. | |
| 5,405,072 A | 4/1995 | Zlock et al. | |
| 5,413,267 A | 5/1995 | Solyntjes et al. | |
| 5,413,268 A | 5/1995 | Green et al. | |
| 5,413,272 A | 5/1995 | Green et al. | |
| 5,415,335 A | 5/1995 | Knodell, Jr. | |
| 5,417,203 A | 5/1995 | Tovey et al. | |
| 5,417,361 A | 5/1995 | Williamson, IV | |
| 5,425,745 A | 6/1995 | Green et al. | |
| 5,431,322 A | 7/1995 | Green et al. | |
| 5,431,654 A | 7/1995 | Nic | |
| 5,433,721 A | 7/1995 | Hooven et al. | |
| 5,437,681 A | 8/1995 | Meade et al. | |
| 5,445,304 A | 8/1995 | Plyley et al. | |
| 5,456,401 A | 10/1995 | Green et al. | |
| 5,462,215 A | 10/1995 | Viola et al. | |
| 5,465,894 A | 11/1995 | Clark et al. | |
| 5,465,895 A | 11/1995 | Knodel et al. | |
| 5,465,896 A | 11/1995 | Allen et al. | |
| 5,470,006 A | 11/1995 | Rodak | |
| 5,472,132 A | 12/1995 | Savage et al. | |
| 5,474,566 A | 12/1995 | Alesi et al. | |
| 5,478,354 A | 12/1995 | Tovey et al. | |
| 5,480,089 A | 1/1996 | Blewett | |
| 5,482,197 A | 1/1996 | Green et al. | |
| 5,484,095 A | 1/1996 | Green et al. | |
| 5,484,451 A | 1/1996 | Akopov et al. | |
| 5,485,947 A | 1/1996 | Olson et al. | |
| 5,485,952 A | 1/1996 | Fontayne | |
| 5,487,499 A | 1/1996 | Sorrentino et al. | |
| 5,487,500 A | 1/1996 | Knodel et al. | |
| 5,489,058 A | 2/1996 | Plyley et al. | |
| 5,497,933 A | 3/1996 | DeFonzo et al. | |
| 5,503,320 A | 4/1996 | Webster et al. | |
| 5,505,363 A | 4/1996 | Green et al. | |
| 5,509,596 A | 4/1996 | Green et al. | |
| 5,514,157 A | 5/1996 | Nicholas et al. | |
| 5,518,163 A | 5/1996 | Hooven | |
| 5,518,164 A | 5/1996 | Hooven | |
| 5,520,700 A | 5/1996 | Beyar et al. | |
| 5,522,817 A | 6/1996 | Sander et al. | |
| 5,529,235 A | 6/1996 | Boiarski et al. | |
| 5,533,661 A | 7/1996 | Main et al. | |
| 5,535,934 A | 7/1996 | Boiarski et al. | |
| 5,535,935 A | 7/1996 | Vidal et al. | |
| 5,535,937 A | 7/1996 | Boiarski et al. | |
| 5,540,375 A | 7/1996 | Bolanos et al. | |
| 5,542,594 A | 8/1996 | McKean et al. | |
| 5,547,117 A | 8/1996 | Hamblin et al. | |
| 5,553,765 A | 9/1996 | Knodel et al. | |
| 5,554,169 A | 9/1996 | Green et al. | |
| 5,560,530 A | 10/1996 | Bolanos et al. | |
| 5,560,532 A | 10/1996 | DeFonzo et al. | |
| 5,562,239 A | 10/1996 | Boiarski et al. | |
| 5,562,241 A | 10/1996 | Knodel et al. | |
| 5,562,682 A | 10/1996 | Oberlin et al. | |
| 5,564,615 A | 10/1996 | Bishop et al. | |
| 5,571,116 A | 11/1996 | Bolanos et al. | |
| 5,575,799 A | 11/1996 | Bolanos et al. | |
| 5,577,654 A | 11/1996 | Bishop | |
| 5,579,978 A | 12/1996 | Green et al. | |
| 5,580,067 A | 12/1996 | Hamblin et al. | |
| 5,584,425 A | 12/1996 | Savage et al. | |
| 5,586,711 A | 12/1996 | Plyley et al. | |
| 5,588,579 A | 12/1996 | Schnut et al. | |
| 5,588,580 A | 12/1996 | Paul et al. | |
| 5,588,581 A | 12/1996 | Conlon et al. | |
| 5,597,107 A | 1/1997 | Knodel et al. | |
| 5,601,224 A | 2/1997 | Bishop et al. | |
| 5,603,443 A | 2/1997 | Clark et al. | |
| 5,605,272 A | 2/1997 | Witt et al. | |
| 5,605,273 A | 2/1997 | Hamblin et al. | |
| 5,607,094 A | 3/1997 | Clark et al. | |
| 5,607,095 A | 3/1997 | Smith et al. | |
| 5,609,285 A | 3/1997 | Grant et al. | |

| | | |
|---|---|---|
| 5,609,601 A | 3/1997 | Kolesa et al. |
| 5,624,452 A | 4/1997 | Yates |
| 5,626,587 A | 5/1997 | Bishop et al. |
| 5,628,446 A | 5/1997 | Geiste et al. |
| 5,630,539 A | 5/1997 | Plyley et al. |
| 5,630,540 A | 5/1997 | Blewett |
| 5,632,432 A | 5/1997 | Schulze et al. |
| 5,632,433 A | 5/1997 | Grant et al. |
| 5,634,584 A | 6/1997 | Okorocha et al. |
| 5,636,779 A | 6/1997 | Palmer |
| 5,636,780 A | 6/1997 | Green et al. |
| 5,639,008 A | 6/1997 | Gallagher et al. |
| 5,645,209 A | 7/1997 | Green et al. |
| 5,647,526 A | 7/1997 | Green et al. |
| 5,649,937 A | 7/1997 | Bito et al. |
| 5,651,491 A | 7/1997 | Heaton et al. |
| 5,653,373 A | 8/1997 | Green et al. |
| 5,653,374 A | 8/1997 | Young et al. |
| 5,655,698 A | 8/1997 | Yoon |
| 5,657,921 A | 8/1997 | Young et al. |
| 5,662,258 A | 9/1997 | Knodel et al. |
| 5,662,260 A | 9/1997 | Yoon |
| 5,667,517 A | 9/1997 | Hooven |
| 5,667,527 A | 9/1997 | Cook |
| 5,669,544 A | 9/1997 | Schulze et al. |
| 5,669,918 A | 9/1997 | Balazs et al. |
| 5,673,840 A | 10/1997 | Schulze et al. |
| 5,673,841 A | 10/1997 | Schulze et al. |
| 5,673,842 A | 10/1997 | Bittner et al. |
| 5,678,748 A | 10/1997 | Plyley et al. |
| 5,680,981 A | 10/1997 | Mililli et al. |
| 5,680,982 A | 10/1997 | Schulze et al. |
| 5,680,983 A | 10/1997 | Plyley et al. |
| 5,685,474 A | 11/1997 | Seeber |
| 5,688,270 A | 11/1997 | Yates et al. |
| 5,690,269 A | 11/1997 | Bolanos et al. |
| 5,692,668 A | 12/1997 | Schulze et al. |
| 5,697,543 A | 12/1997 | Burdorff |
| 5,702,408 A | 12/1997 | Wales et al. |
| 5,704,534 A | 1/1998 | Huitema et al. |
| 5,706,997 A | 1/1998 | Green et al. |
| 5,706,998 A | 1/1998 | Plyley et al. |
| 5,709,334 A | 1/1998 | Sorrentino et al. |
| 5,709,680 A | 1/1998 | Yates et al. |
| 5,711,472 A | 1/1998 | Bryan |
| 5,713,505 A | 2/1998 | Huitema |
| 5,715,987 A | 2/1998 | Kelley et al. |
| 5,715,988 A | 2/1998 | Palmer |
| 5,716,366 A | 2/1998 | Yates |
| 5,718,359 A | 2/1998 | Palmer et al. |
| 5,718,360 A | 2/1998 | Green et al. |
| 5,725,536 A | 3/1998 | Oberlin et al. |
| 5,725,554 A | 3/1998 | Simon et al. |
| 5,730,758 A | 3/1998 | Allgeyer |
| 5,732,821 A | 3/1998 | Stone et al. |
| 5,732,871 A | 3/1998 | Clark et al. |
| 5,732,872 A | 3/1998 | Bolduc et al. |
| 5,735,445 A | 4/1998 | Vidal et al. |
| 5,743,456 A | 4/1998 | Jones et al. |
| 5,752,644 A | 5/1998 | Bolanos et al. |
| 5,758,814 A | 6/1998 | Gallagher et al. |
| 5,762,255 A | 6/1998 | Chrisman et al. |
| 5,762,256 A | 6/1998 | Mastri et al. |
| 5,779,130 A | 7/1998 | Alesi et al. |
| 5,779,131 A | 7/1998 | Knodel et al. |
| 5,779,132 A | 7/1998 | Knodel et al. |
| 5,782,396 A | 7/1998 | Mastri et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,799,857 A | 9/1998 | Robertson et al. |
| 5,820,009 A | 10/1998 | Melling et al. |
| 5,823,066 A | 10/1998 | Huitema et al. |
| 5,826,776 A | 10/1998 | Schulze et al. |
| 5,829,662 A | 11/1998 | Allen et al. |
| 5,833,690 A | 11/1998 | Yates et al. |
| 5,833,695 A | 11/1998 | Yoon |
| 5,836,503 A | 11/1998 | Ehrenfels et al. |
| 5,836,960 A | 11/1998 | Kolesa et al. |
| 5,839,639 A | 11/1998 | Sauer et al. |
| 5,855,311 A | 1/1999 | Hamblin et al. |
| 5,865,361 A | 2/1999 | Milliman et al. |
| 5,868,760 A | 2/1999 | McGuckin, Jr. |
| 5,871,135 A | 2/1999 | Williamson, IV et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,897,562 A | 4/1999 | Bolanos et al. |
| 5,901,895 A | 5/1999 | Heaton et al. |
| 5,904,693 A | 5/1999 | Dicesare et al. |
| 5,908,427 A | 6/1999 | McKean et al. |
| 5,911,353 A | 6/1999 | Bolanos et al. |
| 5,915,616 A | 6/1999 | Viola et al. |
| 5,918,791 A | 7/1999 | Sorrentino et al. |
| 5,919,198 A | 7/1999 | Graves, Jr. et al. |
| 5,941,442 A | 8/1999 | Geiste et al. |
| 5,954,259 A | 9/1999 | Viola et al. |
| 5,988,479 A | 11/1999 | Palmer |
| 6,010,054 A | 1/2000 | Johnson et al. |
| 6,017,356 A | 1/2000 | Frederick et al. |
| 6,022,352 A | 2/2000 | Vandewalle |
| 6,032,849 A | 3/2000 | Mastri et al. |
| 6,045,560 A | 4/2000 | McKean et al. |
| 6,047,861 A | 4/2000 | Vidal et al. |
| 6,050,472 A | 4/2000 | Shibata |
| 6,053,390 A | 4/2000 | Green et al. |
| 6,062,360 A * | 5/2000 | Shields .......................... 192/21 |
| 6,079,606 A | 6/2000 | Milliman et al. |
| 6,083,234 A | 7/2000 | Nicholas et al. |
| 6,083,242 A | 7/2000 | Cook |
| 6,086,600 A | 7/2000 | Kortenbach |
| 6,099,551 A | 8/2000 | Gabbay |
| 6,102,271 A | 8/2000 | Longo et al. |
| 6,109,500 A | 8/2000 | Alli et al. |
| 6,119,913 A | 9/2000 | Adams et al. |
| H1904 H | 10/2000 | Yates et al. |
| 6,126,058 A | 10/2000 | Adams et al. |
| 6,131,789 A | 10/2000 | Schulze et al. |
| 6,155,473 A | 12/2000 | Tompkins et al. |
| 6,171,330 B1 | 1/2001 | Benchetrit |
| 6,193,129 B1 | 2/2001 | Bittner et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,264,086 B1 | 7/2001 | McGuckin, Jr. |
| 6,264,087 B1 | 7/2001 | Whitman |
| 6,273,897 B1 | 8/2001 | Dalessandro et al. |
| 6,302,311 B1 | 10/2001 | Adams et al. |
| 6,315,184 B1 | 11/2001 | Whitman |
| 6,320,123 B1 | 11/2001 | Reimers |
| 6,330,965 B1 | 12/2001 | Milliman et al. |
| 6,358,224 B1 | 3/2002 | Tims et al. |
| 6,370,981 B2 | 4/2002 | Watarai |
| 6,387,113 B1 | 5/2002 | Hawkins et al. |
| 6,416,486 B1 | 7/2002 | Wampler |
| RE37,814 E | 8/2002 | Allgeyer |
| 6,436,107 B1 | 8/2002 | Wang et al. |
| 6,439,439 B1 | 8/2002 | Rickard et al. |
| 6,443,973 B1 | 9/2002 | Whitman |
| 6,488,196 B1 | 12/2002 | Fenton, Jr. |
| 6,488,197 B1 | 12/2002 | Whitman |
| 6,491,201 B1 | 12/2002 | Whitman |
| 6,505,768 B2 | 1/2003 | Whitman |
| 6,517,565 B1 | 2/2003 | Whitman et al. |
| 6,522,101 B2 | 2/2003 | Malackowski |
| 6,569,171 B2 | 5/2003 | DeGuillebon et al. |
| 6,578,751 B2 | 6/2003 | Hartwick |
| 6,588,643 B2 | 7/2003 | Bolduc et al. |
| 6,601,749 B2 | 8/2003 | Sullivan et al. |
| 6,616,686 B2 | 9/2003 | Coleman et al. |
| 6,619,529 B2 | 9/2003 | Green et al. |
| 6,629,630 B2 | 10/2003 | Adams |
| 6,629,988 B2 | 10/2003 | Weadock |
| 6,644,532 B2 | 11/2003 | Green et al. |

| | | |
|---|---|---|
| 6,669,073 B2 | 12/2003 | Milliman et al. |
| 6,681,978 B2 | 1/2004 | Geiste et al. |
| 6,681,979 B2 | 1/2004 | Whitman |
| 6,695,199 B2 | 2/2004 | Whitman |
| 6,698,643 B2 | 3/2004 | Whitman |
| 6,716,233 B1 | 4/2004 | Whitman |
| 6,755,338 B2 | 6/2004 | Hahnen et al. |
| 6,769,594 B2 | 8/2004 | Orban, III |
| 6,773,438 B1 | 8/2004 | Knodel et al. |
| 6,786,382 B1 | 9/2004 | Hoffman |
| 6,793,652 B1 | 9/2004 | Whitman et al. |
| 6,805,273 B2 | 10/2004 | Bilotti et al. |
| 6,817,508 B1 | 11/2004 | Racenet et al. |
| 6,817,509 B2 | 11/2004 | Geiste et al. |
| 6,817,974 B2 | 11/2004 | Cooper et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| RE38,708 E | 3/2005 | Bolanos et al. |
| 6,874,669 B2 | 4/2005 | Adams et al. |
| 6,877,647 B2 | 4/2005 | Green et al. |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,960,107 B1 * | 11/2005 | Schaub et al. ............... 440/75 |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,981,628 B2 | 1/2006 | Wales |
| 6,981,941 B2 | 1/2006 | Whitman et al. |
| 6,986,451 B1 | 1/2006 | Mastri et al. |
| 6,988,649 B2 | 1/2006 | Shelton, IV et al. |
| 6,988,650 B2 | 1/2006 | Schwemberger et al. |
| 6,997,931 B2 | 2/2006 | Sauer et al. |
| 7,000,818 B2 | 2/2006 | Shelton, IV et al. |
| 7,000,819 B2 | 2/2006 | Swayze et al. |
| 7,008,435 B2 | 3/2006 | Cummins |
| 7,032,798 B2 | 4/2006 | Whitman et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,056,330 B2 | 6/2006 | Gayton |
| 7,066,944 B2 | 6/2006 | Laufer et al. |
| 7,070,083 B2 | 7/2006 | Jankowski |
| 7,077,856 B2 | 7/2006 | Whitman |
| 7,080,769 B2 | 7/2006 | Vresh et al. |
| 7,083,075 B2 | 8/2006 | Swayze et al. |
| 7,090,684 B2 | 8/2006 | McGuckin, Jr. et al. |
| 7,097,089 B2 | 8/2006 | Marczyk |
| 7,108,709 B2 | 9/2006 | Cummins |
| 7,111,769 B2 | 9/2006 | Wales et al. |
| 7,114,642 B2 | 10/2006 | Whitman |
| 7,118,582 B1 | 10/2006 | Wang et al. |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,139 B2 | 12/2006 | Schwemberger et al. |
| 7,156,863 B2 | 1/2007 | Sonnenschein et al. |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,182,239 B1 | 2/2007 | Myers |
| 7,188,758 B2 | 3/2007 | Viola et al. |
| 7,207,471 B2 | 4/2007 | Heinrich et al. |
| 7,207,472 B2 | 4/2007 | Wukusick et al. |
| 7,210,609 B2 | 5/2007 | Leiboff et al. |
| 7,220,272 B2 | 5/2007 | Weadock |
| 7,225,964 B2 | 6/2007 | Mastri et al. |
| 7,234,624 B2 | 6/2007 | Gresham et al. |
| 7,237,708 B1 | 7/2007 | Guy et al. |
| 7,238,195 B2 | 7/2007 | Viola |
| 7,246,734 B2 | 7/2007 | Shelton, IV |
| 7,258,262 B2 | 8/2007 | Mastri et al. |
| 7,278,562 B2 | 10/2007 | Mastri et al. |
| 7,278,563 B1 | 10/2007 | Green |
| 7,296,724 B2 | 11/2007 | Green et al. |
| 7,297,149 B2 | 11/2007 | Vitali et al. |
| 7,303,106 B2 | 12/2007 | Milliman et al. |
| 7,303,107 B2 | 12/2007 | Milliman et al. |
| 7,303,108 B2 | 12/2007 | Shelton, IV |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,343,920 B2 | 3/2008 | Toby et al. |
| 7,364,060 B2 | 4/2008 | Milliman |
| 7,364,061 B2 | 4/2008 | Swayze et al. |
| 7,380,695 B2 | 6/2008 | Doll et al. |
| 7,398,907 B2 | 7/2008 | Racenet et al. |
| 7,398,908 B2 | 7/2008 | Holsten et al. |
| 7,404,508 B2 | 7/2008 | Smith et al. |
| 7,404,509 B2 | 7/2008 | Ortiz et al. |
| 7,410,086 B2 | 8/2008 | Ortiz et al. |
| 7,419,080 B2 | 9/2008 | Smith et al. |
| 7,422,136 B1 | 9/2008 | Marczyk |
| 7,424,965 B2 | 9/2008 | Racenet et al. |
| 7,431,188 B1 | 10/2008 | Marczyk |
| 7,431,730 B2 | 10/2008 | Viola |
| 7,434,715 B2 | 10/2008 | Shelton, IV et al. |
| 7,438,209 B1 | 10/2008 | Hess et al. |
| 7,441,685 B2 | 10/2008 | Boudreaux |
| 7,455,208 B2 | 11/2008 | Wales et al. |
| 7,461,767 B2 | 12/2008 | Viola et al. |
| 7,464,847 B2 | 12/2008 | Viola et al. |
| 7,472,814 B2 | 1/2009 | Mastri et al. |
| 7,481,347 B2 | 1/2009 | Roy |
| 7,481,349 B2 | 1/2009 | Holsten et al. |
| 7,481,824 B2 | 1/2009 | Boudreaux et al. |
| 7,490,749 B2 | 2/2009 | Schall et al. |
| 7,494,039 B2 | 2/2009 | Racenet et al. |
| 7,506,790 B2 | 3/2009 | Shelton, IV |
| 7,510,107 B2 | 3/2009 | Timm et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,559,450 B2 | 7/2009 | Wales et al. |
| 7,568,604 B2 | 8/2009 | Ehrenfels et al. |
| 7,575,144 B2 | 8/2009 | Ortiz et al. |
| 7,588,175 B2 | 9/2009 | Timm et al. |
| 7,588,176 B2 | 9/2009 | Timm et al. |
| 7,597,229 B2 | 10/2009 | Boudreaux et al. |
| 7,600,663 B2 | 10/2009 | Green |
| 7,604,150 B2 | 10/2009 | Boudreaux |
| 7,604,151 B2 | 10/2009 | Hess et al. |
| 7,631,793 B2 | 12/2009 | Rethy et al. |
| 7,641,092 B2 | 1/2010 | Kruszynski et al. |
| 7,641,093 B2 | 1/2010 | Doll et al. |
| 7,658,311 B2 | 2/2010 | Boudreaux |
| 7,665,646 B2 | 2/2010 | Prommersberger |
| 7,669,747 B2 | 3/2010 | Weisenburgh, II et al. |
| 7,673,782 B2 | 3/2010 | Hess et al. |
| 7,699,204 B2 | 4/2010 | Viola |
| 7,717,312 B2 | 5/2010 | Beetel |
| 7,721,930 B2 | 5/2010 | McKenna et al. |
| 7,726,537 B2 | 6/2010 | Olson et al. |
| 7,726,538 B2 | 6/2010 | Holsten et al. |
| 7,731,072 B2 | 6/2010 | Timm et al. |
| 7,735,703 B2 | 6/2010 | Morgan et al. |
| 7,743,960 B2 | 6/2010 | Whitman et al. |
| 7,753,245 B2 | 7/2010 | Boudreaux et al. |
| 7,766,209 B2 | 8/2010 | Baxter, III et al. |
| 7,780,054 B2 | 8/2010 | Wales |
| 7,784,662 B2 | 8/2010 | Wales et al. |
| 7,793,812 B2 | 9/2010 | Moore et al. |
| 7,798,386 B2 | 9/2010 | Schall et al. |

| Patent/Publication No. | Date | Inventor(s) |
|---|---|---|
| 7,810,692 B2 | 10/2010 | Hall et al. |
| 7,810,693 B2 | 10/2010 | Broehl et al. |
| 7,819,296 B2 | 10/2010 | Hueil et al. |
| 7,819,297 B2 | 10/2010 | Doll et al. |
| 7,819,298 B2 | 10/2010 | Hall et al. |
| 7,819,299 B2 | 10/2010 | Shelton, IV et al. |
| 7,832,408 B2 | 11/2010 | Shelton, IV et al. |
| 7,832,611 B2 | 11/2010 | Boyden et al. |
| 7,832,612 B2 | 11/2010 | Baxter, III et al. |
| 7,837,080 B2 | 11/2010 | Schwemberger |
| 7,845,533 B2 | 12/2010 | Marczyk et al. |
| 7,845,534 B2 | 12/2010 | Viola et al. |
| 7,857,185 B2 | 12/2010 | Swayze et al. |
| 7,857,186 B2 | 12/2010 | Baxter, III et al. |
| 7,861,906 B2 | 1/2011 | Doll et al. |
| 7,866,527 B2 | 1/2011 | Hall et al. |
| 7,870,989 B2 | 1/2011 | Viola et al. |
| 7,905,380 B2 | 3/2011 | Shelton, IV et al. |
| 7,905,381 B2 | 3/2011 | Baxter, III et al. |
| 7,909,221 B2 | 3/2011 | Viola et al. |
| 7,913,891 B2 | 3/2011 | Doll et al. |
| 7,918,377 B2 | 4/2011 | Measamer et al. |
| 7,922,061 B2 | 4/2011 | Shelton, IV et al. |
| 7,922,063 B2 | 4/2011 | Zemlok et al. |
| 7,934,630 B2 | 5/2011 | Shelton, Iv et al. |
| 7,950,560 B2 | 5/2011 | Zemlok et al. |
| 7,954,684 B2 | 6/2011 | Boudreaux |
| 7,954,686 B2 | 6/2011 | Baxter, III et al. |
| 7,959,051 B2 | 6/2011 | Smith et al. |
| 7,980,443 B2 | 7/2011 | Scheib et al. |
| 8,002,795 B2 | 8/2011 | Beetel |
| 8,011,551 B2 | 9/2011 | Marczyk et al. |
| 8,020,743 B2 | 9/2011 | Shelton, IV |
| 8,056,787 B2 | 11/2011 | Boudreaux et al. |
| 8,066,167 B2 | 11/2011 | Measamer et al. |
| D650,074 S | 12/2011 | Hunt et al. |
| 8,083,120 B2 | 12/2011 | Shelton, IV et al. |
| 2002/0117534 A1 | 8/2002 | Green et al. |
| 2003/0216778 A1 | 11/2003 | Weadock |
| 2004/0006372 A1 | 1/2004 | Racenet et al. |
| 2004/0028502 A1 | 2/2004 | Cummins |
| 2004/0034369 A1 | 2/2004 | Sauer et al. |
| 2004/0094597 A1 | 5/2004 | Whitman et al. |
| 2004/0097987 A1 | 5/2004 | Pugsley et al. |
| 2004/0108357 A1 | 6/2004 | Milliman et al. |
| 2004/0111081 A1 | 6/2004 | Whitman et al. |
| 2004/0122471 A1 | 6/2004 | Toby et al. |
| 2004/0164123 A1 | 8/2004 | Racenet et al. |
| 2004/0167572 A1 | 8/2004 | Roth et al. |
| 2004/0173659 A1 | 9/2004 | Green et al. |
| 2004/0222268 A1 | 11/2004 | Bilotti et al. |
| 2004/0232199 A1 | 11/2004 | Shelton, IV et al. |
| 2004/0232201 A1 | 11/2004 | Wenchell et al. |
| 2004/0243151 A1 | 12/2004 | Demmy et al. |
| 2004/0243176 A1 | 12/2004 | Hahnen et al. |
| 2004/0254608 A1 | 12/2004 | Huitema et al. |
| 2004/0267310 A1 | 12/2004 | Racenet et al. |
| 2005/0006434 A1 | 1/2005 | Wales et al. |
| 2005/0021026 A1 | 1/2005 | Baily |
| 2005/0059997 A1 | 3/2005 | Bauman et al. |
| 2005/0070958 A1 | 3/2005 | Swayze et al. |
| 2005/0072827 A1 | 4/2005 | Mollenauer |
| 2005/0103819 A1 | 5/2005 | Racenet et al. |
| 2005/0107824 A1 | 5/2005 | Hillstead et al. |
| 2005/0119669 A1 | 6/2005 | Demmy |
| 2005/0125009 A1 | 6/2005 | Perry et al. |
| 2005/0131390 A1 | 6/2005 | Heinrich et al. |
| 2005/0143759 A1 | 6/2005 | Kelly |
| 2005/0145675 A1 | 7/2005 | Hartwick et al. |
| 2005/0165415 A1 | 7/2005 | Wales |
| 2005/0173490 A1 | 8/2005 | Shelton, IV |
| 2005/0184121 A1 | 8/2005 | Heinrich |
| 2005/0187576 A1 | 8/2005 | Whitman et al. |
| 2005/0189397 A1 | 9/2005 | Jankowski |
| 2005/0192628 A1 | 9/2005 | Viola |
| 2005/0203550 A1 | 9/2005 | Laufer et al. |
| 2005/0216055 A1 | 9/2005 | Scirica et al. |
| 2005/0230453 A1 | 10/2005 | Viola |
| 2005/0240222 A1 | 10/2005 | Shipp |
| 2005/0263562 A1 | 12/2005 | Shelton, IV et al. |
| 2005/0263563 A1 | 12/2005 | Racenet et al. |
| 2005/0274768 A1 | 12/2005 | Cummins et al. |
| 2006/0000867 A1* | 1/2006 | Shelton et al. .............. 227/175.1 |
| 2006/0011699 A1 | 1/2006 | Olson et al. |
| 2006/0025813 A1 | 2/2006 | Shelton et al. |
| 2006/0025816 A1 | 2/2006 | Shelton |
| 2006/0047307 A1 | 3/2006 | Ortiz et al. |
| 2006/0049229 A1 | 3/2006 | Milliman et al. |
| 2006/0052825 A1 | 3/2006 | Ransick et al. |
| 2006/0060630 A1 | 3/2006 | Shelton, IV et al. |
| 2006/0085033 A1 | 4/2006 | Criscuolo et al. |
| 2006/0100643 A1 | 5/2006 | Laufer et al. |
| 2006/0108393 A1 | 5/2006 | Heinrich et al. |
| 2006/0122636 A1 | 6/2006 | Bailly et al. |
| 2006/0142772 A1 | 6/2006 | Ralph et al. |
| 2006/0151567 A1 | 7/2006 | Roy |
| 2006/0180634 A1 | 8/2006 | Shelton, IV et al. |
| 2006/0226196 A1 | 10/2006 | Hueil et al. |
| 2006/0235469 A1 | 10/2006 | Viola |
| 2006/0241692 A1 | 10/2006 | McGuckin, Jr. et al. |
| 2006/0278680 A1 | 12/2006 | Viola et al. |
| 2006/0278681 A1 | 12/2006 | Viola et al. |
| 2006/0289602 A1 | 12/2006 | Wales et al. |
| 2007/0023476 A1 | 2/2007 | Whitman et al. |
| 2007/0023477 A1 | 2/2007 | Whitman et al. |
| 2007/0027469 A1 | 2/2007 | Smith et al. |
| 2007/0034666 A1 | 2/2007 | Holsten et al. |
| 2007/0034668 A1 | 2/2007 | Holsten et al. |
| 2007/0045379 A1 | 3/2007 | Shelton, IV |
| 2007/0073340 A1 | 3/2007 | Shelton, IV et al. |
| 2007/0073341 A1 | 3/2007 | Smith |
| 2007/0075114 A1 | 4/2007 | Shelton, IV et al. |
| 2007/0083234 A1 | 4/2007 | Shelton, IV et al. |
| 2007/0084897 A1 | 4/2007 | Shelton, IV et al. |
| 2007/0102452 A1 | 5/2007 | Shelton, IV et al. |
| 2007/0102453 A1 | 5/2007 | Morgan et al. |
| 2007/0102472 A1 | 5/2007 | Shelton, IV |
| 2007/0102473 A1 | 5/2007 | Shelton, IV et al. |
| 2007/0102474 A1 | 5/2007 | Shelton, IV et al. |
| 2007/0102476 A1 | 5/2007 | Shelton, IV et al. |
| 2007/0106317 A1 | 5/2007 | Shelton, IV et al. |
| 2007/0114261 A1 | 5/2007 | Ortiz et al. |
| 2007/0158385 A1 | 7/2007 | Hueil et al. |
| 2007/0170225 A1 | 7/2007 | Shelton, IV et al. |
| 2007/0175949 A1 | 8/2007 | Shelton, IV et al. |
| 2007/0175950 A1 | 8/2007 | Shelton, IV et al. |
| 2007/0175951 A1 | 8/2007 | Shelton, IV et al. |
| 2007/0175952 A1 | 8/2007 | Shelton, IV et al. |
| 2007/0175953 A1 | 8/2007 | Shelton, IV et al. |
| 2007/0175955 A1 | 8/2007 | Shelton, IV et al. |
| 2007/0175956 A1 | 8/2007 | Swayze et al. |
| 2007/0175957 A1 | 8/2007 | Shelton, IV et al. |
| 2007/0175958 A1 | 8/2007 | Shelton, IV et al. |
| 2007/0175959 A1 | 8/2007 | Shelton, IV et al. |
| 2007/0175960 A1 | 8/2007 | Shelton, IV et al. |
| 2007/0175961 A1 | 8/2007 | Shelton, IV et al. |
| 2007/0175962 A1 | 8/2007 | Shelton, IV et al. |
| 2007/0175964 A1 | 8/2007 | Shelton, IV et al. |
| 2007/0179476 A1 | 8/2007 | Shelton, IV et al. |
| 2007/0181632 A1 | 8/2007 | Milliman |
| 2007/0194079 A1 | 8/2007 | Hueil et al. |
| 2007/0194080 A1 | 8/2007 | Swayze et al. |
| 2007/0194081 A1 | 8/2007 | Hueil et al. |
| 2007/0194082 A1 | 8/2007 | Morgan et al. |
| 2007/0221700 A1 | 9/2007 | Ortiz et al. |
| 2007/0221701 A1 | 9/2007 | Ortiz et al. |
| 2007/0225562 A1 | 9/2007 | Spivey et al. |
| 2007/0233053 A1 | 10/2007 | Shelton, IV et al. |
| 2007/0246505 A1 | 10/2007 | Pace-Floridia et al. |
| 2007/0262116 A1 | 11/2007 | Hueil et al. |
| 2007/0288044 A1 | 12/2007 | Jinno et al. |
| 2008/0029570 A1 | 2/2008 | Shelton et al. |
| 2008/0029571 A1 | 2/2008 | Shelton et al. |
| 2008/0029572 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0029576 A1 | 2/2008 | Shelton et al. |

| | | | | | | |
|---|---|---|---|---|---|---|
| 2008/0029577 | A1 | 2/2008 | Shelton et al. | 2010/0069942 | A1 | 3/2010 | Shelton, IV |
| 2008/0035701 | A1 | 2/2008 | Racenet et al. | 2010/0072254 | A1 | 3/2010 | Aranyi et al. |
| 2008/0041916 | A1 | 2/2008 | Milliman et al. | 2010/0076474 | A1 | 3/2010 | Yates et al. |
| 2008/0041917 | A1 | 2/2008 | Racenet et al. | 2010/0076475 | A1 | 3/2010 | Yates et al. |
| 2008/0078800 | A1 | 4/2008 | Hess et al. | 2010/0089970 | A1 | 4/2010 | Smith et al. |
| 2008/0078801 | A1 | 4/2008 | Shelton et al. | 2010/0089972 | A1 | 4/2010 | Marczyk |
| 2008/0078802 | A1 | 4/2008 | Hess et al. | 2010/0108741 | A1 | 5/2010 | Hessler et al. |
| 2008/0078803 | A1 | 4/2008 | Shelton et al. | 2010/0127042 | A1 | 5/2010 | Shelton, IV |
| 2008/0078804 | A1 | 4/2008 | Shelton et al. | 2010/0133317 | A1 | 6/2010 | Shelton, IV et al. |
| 2008/0078805 | A1 | 4/2008 | Omaits et al. | 2010/0133318 | A1 | 6/2010 | Boudreaux |
| 2008/0078806 | A1 | 4/2008 | Omaits et al. | 2010/0163598 | A1 | 7/2010 | Belzer |
| 2008/0078807 | A1 | 4/2008 | Hess et al. | 2010/0179382 | A1 | 7/2010 | Shelton, IV et al. |
| 2008/0078808 | A1 | 4/2008 | Hess et al. | 2010/0181364 | A1 | 7/2010 | Shelton, IV et al. |
| 2008/0082115 | A1 | 4/2008 | Morgan et al. | 2010/0193566 | A1 | 8/2010 | Schieb et al. |
| 2008/0082124 | A1 | 4/2008 | Hess et al. | 2010/0193567 | A1 | 8/2010 | Scheib et al. |
| 2008/0082125 | A1 | 4/2008 | Murray et al. | 2010/0193568 | A1 | 8/2010 | Scheib et al. |
| 2008/0082126 | A1 | 4/2008 | Murray et al. | 2010/0193569 | A1 | 8/2010 | Yates et al. |
| 2008/0083813 | A1 | 4/2008 | Zemlok et al. | 2010/0198220 | A1 | 8/2010 | Boudreaux et al. |
| 2008/0140115 | A1 | 6/2008 | Stopek | 2010/0200637 | A1 | 8/2010 | Beetel |
| 2008/0164296 | A1 | 7/2008 | Shelton et al. | 2010/0213241 | A1 | 8/2010 | Bedi et al. |
| 2008/0167522 | A1 | 7/2008 | Giordano et al. | 2010/0222901 | A1 | 9/2010 | Swayze et al. |
| 2008/0167644 | A1 | 7/2008 | Shelton et al. | 2010/0224669 | A1 | 9/2010 | Shelton, IV et al. |
| 2008/0167670 | A1 | 7/2008 | Shelton et al. | 2010/0243707 | A1 | 9/2010 | Olson et al. |
| 2008/0167671 | A1 | 7/2008 | Giordano et al. | 2010/0243708 | A1 | 9/2010 | Aranyi et al. |
| 2008/0167672 | A1 | 7/2008 | Giordano et al. | 2010/0243709 | A1 | 9/2010 | Hess et al. |
| 2008/0167736 | A1 | 7/2008 | Swayze et al. | 2010/0264193 | A1 | 10/2010 | Huang et al. |
| 2008/0169327 | A1 | 7/2008 | Shelton et al. | 2010/0264194 | A1 | 10/2010 | Huang et al. |
| 2008/0169328 | A1 | 7/2008 | Shelton | 2010/0276471 | A1 | 11/2010 | Whitman |
| 2008/0169329 | A1 | 7/2008 | Shelton et al. | 2010/0294827 | A1 | 11/2010 | Boyden et al. |
| 2008/0169330 | A1 | 7/2008 | Shelton et al. | 2010/0294829 | A1 | 11/2010 | Giordano et al. |
| 2008/0169331 | A1 | 7/2008 | Shelton et al. | 2010/0301095 | A1 | 12/2010 | Shelton, IV et al. |
| 2008/0169332 | A1 | 7/2008 | Shelton et al. | 2010/0301096 | A1 | 12/2010 | Moore et al. |
| 2008/0169333 | A1 | 7/2008 | Shelton et al. | 2010/0305552 | A1 | 12/2010 | Shelton, IV et al. |
| 2008/0183193 | A1 | 7/2008 | Omori et al. | 2010/0308100 | A1 | 12/2010 | Boudreaux |
| 2008/0197167 | A1 | 8/2008 | Viola et al. | 2011/0006099 | A1 | 1/2011 | Hall et al. |
| 2008/0251568 | A1 | 10/2008 | Zemlok et al. | 2011/0006101 | A1 | 1/2011 | Hall et al. |
| 2008/0283570 | A1 | 11/2008 | Boyden et al. | 2011/0006103 | A1 | 1/2011 | Laurent et al. |
| 2008/0290134 | A1 | 11/2008 | Bettuchi et al. | 2011/0011914 | A1 | 1/2011 | Baxter, III et al. |
| 2008/0296346 | A1 | 12/2008 | Shelton, IV et al. | 2011/0011915 | A1 | 1/2011 | Shelton, IV |
| 2008/0300580 | A1 | 12/2008 | Shelton, IV et al. | 2011/0017801 | A1 | 1/2011 | Zemlok et al. |
| 2008/0308602 | A1 | 12/2008 | Timm et al. | 2011/0024477 | A1 | 2/2011 | Hall et al. |
| 2008/0308603 | A1 | 12/2008 | Shelton, IV et al. | 2011/0024478 | A1 | 2/2011 | Shelton, IV |
| 2008/0308608 | A1 | 12/2008 | Prommersberger | 2011/0024479 | A1 | 2/2011 | Swensgard et al. |
| 2008/0314960 | A1 | 12/2008 | Marczyk et al. | 2011/0036887 | A1 | 2/2011 | Zemlok et al. |
| 2009/0001121 | A1 | 1/2009 | Hess et al. | 2011/0042441 | A1 | 2/2011 | Shelton, IV et al. |
| 2009/0001122 | A1 | 1/2009 | Prommersberger et al. | 2011/0060363 | A1 | 3/2011 | Hess et al. |
| 2009/0001124 | A1 | 1/2009 | Hess et al. | 2011/0062212 | A1 | 3/2011 | Shelton, IV et al. |
| 2009/0001130 | A1 | 1/2009 | Hess et al. | 2011/0068145 | A1 | 3/2011 | Bedi et al. |
| 2009/0005807 | A1 | 1/2009 | Hess et al. | 2011/0068148 | A1 | 3/2011 | Hall et al. |
| 2009/0005808 | A1 | 1/2009 | Hess et al. | 2011/0084112 | A1 | 4/2011 | Kostrzewski |
| 2009/0005809 | A1 | 1/2009 | Hess et al. | 2011/0084113 | A1 | 4/2011 | Bedi et al. |
| 2009/0012556 | A1 | 1/2009 | Boudreaux et al. | 2011/0084115 | A1 | 4/2011 | Bedi et al. |
| 2009/0057369 | A1 | 3/2009 | Smith et al. | 2011/0087276 | A1 | 4/2011 | Bedi et al. |
| 2009/0076534 | A1 | 3/2009 | Shelton, IV et al. | 2011/0101065 | A1 | 5/2011 | Milliman |
| 2009/0090763 | A1 | 4/2009 | Zemlok et al. | 2011/0114697 | A1 | 5/2011 | Baxter, III et al. |
| 2009/0108048 | A1 | 4/2009 | Zemlok et al. | 2011/0114698 | A1 | 5/2011 | Baxter, III et al. |
| 2009/0114701 | A1 | 5/2009 | Zemlok et al. | 2011/0114699 | A1 | 5/2011 | Baxter, III et al. |
| 2009/0149871 | A9 | 6/2009 | Kagan et al. | 2011/0114700 | A1 | 5/2011 | Baxter, III et al. |
| 2009/0206125 | A1 | 8/2009 | Huitema et al. | 2011/0118761 | A1 | 5/2011 | Baxter, III et al. |
| 2009/0206126 | A1 | 8/2009 | Huitema et al. | 2011/0121051 | A1 | 5/2011 | Shelton, IV et al. |
| 2009/0206131 | A1 | 8/2009 | Weisenburgh, II et al. | 2011/0121052 | A1 | 5/2011 | Shelton, IV et al. |
| 2009/0206132 | A1 | 8/2009 | Hueil et al. | 2011/0125176 | A1 | 5/2011 | Yates et al. |
| 2009/0206133 | A1 | 8/2009 | Morgan et al. | 2011/0125177 | A1 | 5/2011 | Yates et al. |
| 2009/0206137 | A1 | 8/2009 | Hall et al. | 2011/0132962 | A1 | 6/2011 | Hall et al. |
| 2009/0206139 | A1 | 8/2009 | Hall et al. | 2011/0132963 | A1 | 6/2011 | Giordano et al. |
| 2009/0206141 | A1 | 8/2009 | Huitema et al. | 2011/0132964 | A1 | 6/2011 | Weisenburgh, II et al. |
| 2009/0206142 | A1 | 8/2009 | Huitema et al. | 2011/0132965 | A1 | 6/2011 | Moore et al. |
| 2009/0206143 | A1 | 8/2009 | Huitema et al. | 2011/0139852 | A1 | 6/2011 | Zingman |
| 2009/0209946 | A1 | 8/2009 | Swayze et al. | 2011/0144430 | A1 | 6/2011 | Spivey et al. |
| 2009/0218384 | A1 | 9/2009 | Aranyi | 2011/0147433 | A1 | 6/2011 | Shelton, IV et al. |
| 2009/0242610 | A1 | 10/2009 | Shelton, IV et al. | 2011/0147434 | A1 | 6/2011 | Hueil et al. |
| 2009/0255974 | A1 | 10/2009 | Viola | 2011/0155780 | A1 | 6/2011 | Boudreaux |
| 2009/0255975 | A1 | 10/2009 | Zemlok et al. | 2011/0155781 | A1 | 6/2011 | Swensgard et al. |
| 2009/0255976 | A1 | 10/2009 | Marczyk et al. | 2011/0155785 | A1 | 6/2011 | Laurent et al. |
| 2009/0255977 | A1 | 10/2009 | Zemlok | 2011/0155787 | A1 | 6/2011 | Baxter, III et al. |
| 2009/0255978 | A1 | 10/2009 | Viola et al. | 2011/0163147 | A1 | 7/2011 | Laurent et al. |
| 2009/0308907 | A1 | 12/2009 | Nalagatla et al. | 2011/0174860 | A1 | 7/2011 | Shelton, IV et al. |
| 2010/0012704 | A1 | 1/2010 | Tarinelli Racenet et al. | 2011/0174863 | A1 | 7/2011 | Shelton, IV et al. |
| 2010/0032470 | A1 | 2/2010 | Hess et al. | 2011/0192882 | A1 | 8/2011 | Hess et al. |

| | | | |
|---|---|---|---|
| 2011/0226837 A1 | 9/2011 | Baxter, III et al. | |
| 2011/0233258 A1 | 9/2011 | Boudreaux | |
| 2011/0253766 A1 | 10/2011 | Baxter, III et al. | |
| 2011/0288573 A1 | 11/2011 | Yates et al. | |
| 2011/0290851 A1 | 12/2011 | Shelton, IV | |
| 2011/0290853 A1 | 12/2011 | Shelton, IV et al. | |
| 2011/0290854 A1 | 12/2011 | Timm et al. | |
| 2011/0290855 A1 | 12/2011 | Moore et al. | |
| 2011/0290856 A1 | 12/2011 | Shelton, IV et al. | |
| 2011/0290857 A1 | 12/2011 | Shelton, IV et al. | |
| 2011/0295242 A1 | 12/2011 | Spivey et al. | |
| 2011/0295269 A1 | 12/2011 | Swensgard et al. | |
| 2011/0295270 A1 | 12/2011 | Giordano et al. | |
| 2011/0295295 A1 | 12/2011 | Shelton, IV et al. | |
| 2012/0024934 A1 | 2/2012 | Shelton, IV et al. | |
| 2012/0024935 A1 | 2/2012 | Shelton, IV et al. | |
| 2012/0024936 A1 | 2/2012 | Baxter, III et al. | |
| 2012/0029272 A1 | 2/2012 | Shelton, IV et al. | |
| 2012/0029544 A1 | 2/2012 | Shelton, IV et al. | |
| 2012/0029547 A1 | 2/2012 | Shelton, IV et al. | |

FOREIGN PATENT DOCUMENTS

| | | | |
|---|---|---|---|
| CA | 2512960 A1 | 1/2006 | |
| CA | 2514274 A1 | 1/2006 | |
| CN | 1868411 A | 11/2006 | |
| CN | 1915180 A | 2/2007 | |
| DE | 273689 C | 5/1914 | |
| DE | 1775926 A | 1/1972 | |
| DE | 3036217 A1 | 4/1982 | |
| DE | 3210466 A1 | 9/1983 | |
| DE | 9412228 U | 9/1994 | |
| DE | 19509116 A1 | 9/1996 | |
| DE | 19851291 A1 | 1/2000 | |
| DE | 19924311 A1 | 11/2000 | |
| DE | 69328576 T2 | 1/2001 | |
| DE | 10052679 A1 | 5/2001 | |
| DE | 20112837 U1 | 10/2001 | |
| DE | 20121753 U1 | 4/2003 | |
| DE | 10314072 A1 | 10/2004 | |
| DE | 202007003114 U1 | 6/2007 | |
| EP | 0122046 A1 | 10/1984 | |
| EP | 0070230 B1 | 10/1985 | |
| EP | 0387980 B1 | 10/1985 | |
| EP | 0033548 B1 | 5/1986 | |
| EP | 0276104 A2 | 7/1988 | |
| EP | 0248844 B1 | 1/1993 | |
| EP | 0545029 A1 | 6/1993 | |
| EP | 0277959 B1 | 10/1993 | |
| EP | 0233940 B1 | 11/1993 | |
| EP | 0261230 B1 | 11/1993 | |
| EP | 0639349 A2 | 2/1994 | |
| EP | 0324636 B1 | 3/1994 | |
| EP | 0593920 A1 | 4/1994 | |
| EP | 0523174 B1 | 6/1994 | |
| EP | 0600182 A2 | 6/1994 | |
| EP | 0310431 B1 | 11/1994 | |
| EP | 0375302 B1 | 11/1994 | |
| EP | 0376562 B1 | 11/1994 | |
| EP | 0630612 A1 | 12/1994 | |
| EP | 0634144 A1 | 1/1995 | |
| EP | 0646356 A2 | 4/1995 | |
| EP | 0646357 A1 | 4/1995 | |
| EP | 0653189 A2 | 5/1995 | |
| EP | 0669104 A1 | 8/1995 | |
| EP | 0511470 B1 | 10/1995 | |
| EP | 0679367 A2 | 11/1995 | |
| EP | 0392547 B1 | 12/1995 | |
| EP | 0685204 A1 | 12/1995 | |
| EP | 0364216 B1 | 1/1996 | |
| EP | 0699418 A1 | 3/1996 | |
| EP | 0702937 A1 | 3/1996 | |
| EP | 0705571 A1 | 4/1996 | |
| EP | 0711611 A2 | 5/1996 | |
| EP | 0484677 B2 | 6/1996 | |
| EP | 0541987 B1 | 7/1996 | |
| EP | 0667119 B1 | 7/1996 | |
| EP | 0708618 B1 | 3/1997 | |
| EP | 0770355 A1 | 5/1997 | |
| EP | 0503662 B1 | 6/1997 | |
| EP | 0447121 B1 | 7/1997 | |
| EP | 0625077 B1 | 7/1997 | |
| EP | 0633749 B1 | 8/1997 | |
| EP | 0710090 B1 | 8/1997 | |
| EP | 0578425 B1 | 9/1997 | |
| EP | 0625335 B1 | 11/1997 | |
| EP | 0552423 B1 | 1/1998 | |
| EP | 0592244 B1 | 1/1998 | |
| EP | 0648476 B1 | 1/1998 | |
| EP | 0649290 B1 | 3/1998 | |
| EP | 0598618 B1 | 9/1998 | |
| EP | 0676173 B1 | 9/1998 | |
| EP | 0678007 B1 | 9/1998 | |
| EP | 0603472 B1 | 11/1998 | |
| EP | 0605351 B1 | 11/1998 | |
| EP | 0878169 A1 | 11/1998 | |
| EP | 0879742 A1 | 11/1998 | |
| EP | 0695144 B1 | 12/1998 | |
| EP | 0722296 B1 | 12/1998 | |
| EP | 0760230 B1 | 2/1999 | |
| EP | 0623316 B1 | 3/1999 | |
| EP | 0650701 B1 | 3/1999 | |
| EP | 0537572 B1 | 6/1999 | |
| EP | 0923907 A1 | 6/1999 | |
| EP | 0843906 B1 | 3/2000 | |
| EP | 0552050 B1 | 5/2000 | |
| EP | 0833592 B1 | 5/2000 | |
| EP | 0830094 B1 | 9/2000 | |
| EP | 1034747 A1 | 9/2000 | |
| EP | 1034748 A1 | 9/2000 | |
| EP | 0694290 B1 | 11/2000 | |
| EP | 1050278 A1 | 11/2000 | |
| EP | 1053719 A1 | 11/2000 | |
| EP | 1053720 A1 | 11/2000 | |
| EP | 1055399 A1 | 11/2000 | |
| EP | 1055400 A1 | 11/2000 | |
| EP | 1080694 A1 | 3/2001 | |
| EP | 1090592 A1 | 4/2001 | |
| EP | 1095627 A1 | 5/2001 | |
| EP | 1256318 B1 | 5/2001 | |
| EP | 0806914 B1 | 9/2001 | |
| EP | 0768840 B1 | 12/2001 | |
| EP | 0908152 B1 | 1/2002 | |
| EP | 0872213 B1 | 5/2002 | |
| EP | 0862386 B1 | 6/2002 | |
| EP | 0949886 B1 | 9/2002 | |
| EP | 1238634 A2 | 9/2002 | |
| EP | 0858295 B1 | 12/2002 | |
| EP | 0656188 B1 | 1/2003 | |
| EP | 1284120 A1 | 2/2003 | |
| EP | 1287788 A1 | 3/2003 | |
| EP | 0717966 B1 | 4/2003 | |
| EP | 0869742 B1 | 5/2003 | |
| EP | 0829235 B1 | 6/2003 | |
| EP | 0887046 B1 | 7/2003 | |
| EP | 0852480 B1 | 8/2003 | |
| EP | 0891154 B1 | 9/2003 | |
| EP | 0813843 B1 | 10/2003 | |
| EP | 0873089 B1 | 10/2003 | |
| EP | 0856326 B1 | 11/2003 | |
| EP | 1374788 A1 | 1/2004 | |
| EP | 0741996 B1 | 2/2004 | |
| EP | 0814712 B1 | 2/2004 | |
| EP | 1402837 A1 | 3/2004 | |
| EP | 0705570 B1 | 4/2004 | |
| EP | 0959784 B1 | 4/2004 | |
| EP | 1407719 A2 | 4/2004 | |
| EP | 1086713 B1 | 5/2004 | |
| EP | 0996378 B1 | 6/2004 | |
| EP | 1426012 A1 | 6/2004 | |
| EP | 0833593 B2 | 7/2004 | |
| EP | 1442694 B1 | 8/2004 | |
| EP | 0888749 B1 | 9/2004 | |
| EP | 0959786 B1 | 9/2004 | |
| EP | 1459695 A1 | 9/2004 | |
| EP | 1473819 A1 | 11/2004 | |
| EP | 1477119 A1 | 11/2004 | |
| EP | 1479345 A1 | 11/2004 | |
| EP | 1479347 A1 | 11/2004 | |

| | | | | | | |
|---|---|---|---|---|---|---|
| EP | 1479348 | A1 | 11/2004 | EP | 1749486 B1 | 3/2009 |
| EP | 0754437 | B2 | 12/2004 | EP | 1721576 B1 | 4/2009 |
| EP | 1025807 | B1 | 12/2004 | EP | 1733686 B1 | 4/2009 |
| EP | 1001710 | B1 | 1/2005 | EP | 1745748 B1 | 8/2009 |
| EP | 1520521 | A1 | 4/2005 | EP | 2090256 A2 | 8/2009 |
| EP | 1520523 | A1 | 4/2005 | EP | 1813208 B1 | 11/2009 |
| EP | 1520525 | A1 | 4/2005 | EP | 1607050 B1 | 12/2009 |
| EP | 1522264 | A1 | 4/2005 | EP | 1566150 B1 | 4/2010 |
| EP | 1523942 | A2 | 4/2005 | EP | 1813206 B1 | 4/2010 |
| EP | 1550408 | A1 | 7/2005 | EP | 1769754 B1 | 6/2010 |
| EP | 1557129 | A1 | 7/2005 | EP | 1535565 B1 | 10/2010 |
| EP | 1064883 | B1 | 8/2005 | EP | 1702570 B1 | 10/2010 |
| EP | 1067876 | B1 | 8/2005 | EP | 1785098 B1 | 10/2010 |
| EP | 0870473 | B1 | 9/2005 | EP | 1813205 B1 | 6/2011 |
| EP | 1157666 | B1 | 9/2005 | FR | 999646 A | 2/1952 |
| EP | 0880338 | B1 | 10/2005 | FR | 1112936 A | 3/1956 |
| EP | 1158917 | B1 | 11/2005 | FR | 2765794 A | 1/1999 |
| EP | 1344498 | B1 | 11/2005 | GB | 939929 A | 10/1963 |
| EP | 1330989 | B1 | 12/2005 | GB | 1210522 A | 10/1970 |
| EP | 0771176 | B2 | 1/2006 | GB | 1217159 A | 12/1970 |
| EP | 1621138 | A2 | 2/2006 | GB | 1339394 A | 12/1973 |
| EP | 1621139 | A2 | 2/2006 | GB | 2109241 A | 6/1983 |
| EP | 1621141 | A2 | 2/2006 | GB | 2272159 A | 5/1994 |
| EP | 1621145 | A2 | 2/2006 | GB | 2284242 A | 5/1995 |
| EP | 1621151 | A2 | 2/2006 | GB | 2336214 A | 10/1999 |
| EP | 1034746 | B1 | 3/2006 | GB | 2425903 A | 11/2006 |
| EP | 1632191 | A2 | 3/2006 | JP | 6007357 A | 1/1994 |
| EP | 1065981 | B1 | 5/2006 | JP | 7051273 A | 2/1995 |
| EP | 1082944 | B1 | 5/2006 | JP | 8033641 A | 2/1996 |
| EP | 1652481 | A2 | 5/2006 | JP | 8229050 A | 9/1996 |
| EP | 1382303 | B1 | 6/2006 | JP | 2000033071 A | 2/2000 |
| EP | 1253866 | B1 | 7/2006 | JP | 2000171730 A | 6/2000 |
| EP | 1032318 | B1 | 8/2006 | JP | 2000287987 A | 10/2000 |
| EP | 1045672 | B1 | 8/2006 | JP | 2000325303 A | 11/2000 |
| EP | 1617768 | B1 | 8/2006 | JP | 2001286477 A | 10/2001 |
| EP | 1693015 | A2 | 8/2006 | JP | 2002143078 A | 5/2002 |
| EP | 1400214 | B1 | 9/2006 | JP | 2002369820 A | 12/2002 |
| EP | 1702567 | A2 | 9/2006 | JP | 2005505322 T | 2/2005 |
| EP | 1129665 | B1 | 11/2006 | JP | 2005103293 A | 4/2005 |
| EP | 1400206 | B1 | 11/2006 | JP | 2005131163 A | 5/2005 |
| EP | 1721568 | A1 | 11/2006 | JP | 2005131164 A | 5/2005 |
| EP | 1256317 | B1 | 12/2006 | JP | 2005131173 A | 5/2005 |
| EP | 1728473 | A1 | 12/2006 | JP | 2005131211 A | 5/2005 |
| EP | 1728475 | A2 | 12/2006 | JP | 2005131212 A | 5/2005 |
| EP | 1479346 | B1 | 1/2007 | JP | 2005137423 A | 6/2005 |
| EP | 1484024 | B1 | 1/2007 | JP | 2005152416 A | 6/2005 |
| EP | 1754445 | A2 | 2/2007 | JP | 2006-281405 A | 10/2006 |
| EP | 1759812 | A1 | 3/2007 | RU | 2008830 C1 | 3/1994 |
| EP | 1767163 | A1 | 3/2007 | RU | 2187249 C2 | 8/2002 |
| EP | 1769756 | A1 | 4/2007 | RU | 2225170 C2 | 3/2004 |
| EP | 1769758 | A1 | 4/2007 | SU | 189517 A | 1/1967 |
| EP | 1581128 | B1 | 5/2007 | SU | 328636 A | 9/1972 |
| EP | 1785097 | A2 | 5/2007 | SU | 886900 A | 12/1981 |
| EP | 1790293 | A2 | 5/2007 | SU | 1009439 A | 4/1983 |
| EP | 1800610 | A1 | 6/2007 | SU | 1333319 A2 | 8/1987 |
| EP | 1300117 | B1 | 8/2007 | SU | 1377053 A1 | 2/1988 |
| EP | 1813199 | A1 | 8/2007 | SU | 1561964 A1 | 5/1990 |
| EP | 1813201 | A1 | 8/2007 | SU | 1722476 A1 | 3/1992 |
| EP | 1813203 | A2 | 8/2007 | WO | WO 91/15157 A1 | 10/1991 |
| EP | 1813207 | A1 | 8/2007 | WO | WO 92/20295 A1 | 11/1992 |
| EP | 1813209 | A1 | 8/2007 | WO | WO 92/21300 A1 | 12/1992 |
| EP | 1487359 | B1 | 10/2007 | WO | WO 93/08755 A1 | 5/1993 |
| EP | 1599146 | B1 | 10/2007 | WO | WO 93/13718 A1 | 7/1993 |
| EP | 1839596 | A1 | 10/2007 | WO | WO 93/14690 A1 | 8/1993 |
| EP | 1402821 | B1 | 12/2007 | WO | WO 93/15648 A1 | 8/1993 |
| EP | 1872727 | A1 | 1/2008 | WO | WO 93/15850 A1 | 8/1993 |
| EP | 1897502 | A1 | 3/2008 | WO | WO 93/19681 A1 | 10/1993 |
| EP | 1330201 | B1 | 6/2008 | WO | WO 94/00060 A1 | 1/1994 |
| EP | 1702568 | B1 | 7/2008 | WO | WO 94/11057 A1 | 5/1994 |
| EP | 1943976 | A2 | 7/2008 | WO | WO 94/12108 A1 | 6/1994 |
| EP | 1593337 | B1 | 8/2008 | WO | WO 94/18893 A1 | 9/1994 |
| EP | 1970014 | A1 | 9/2008 | WO | WO 94/22378 A1 | 10/1994 |
| EP | 1980213 | A2 | 10/2008 | WO | WO 94/23659 A1 | 10/1994 |
| EP | 1759645 | B1 | 11/2008 | WO | WO 95/02369 A1 | 1/1995 |
| EP | 1990014 | A2 | 11/2008 | WO | WO 95/03743 A1 | 2/1995 |
| EP | 1693008 | B1 | 12/2008 | WO | WO 95/06817 A1 | 3/1995 |
| EP | 1759640 | B1 | 12/2008 | WO | WO 95/09576 A1 | 4/1995 |
| EP | 2000102 | A2 | 12/2008 | WO | WO 95/09577 A1 | 4/1995 |
| EP | 1736104 | B1 | 3/2009 | WO | WO 95/14436 A1 | 6/1995 |

| | | | | | | |
|---|---|---|---|---|---|---|
| WO | WO 95/17855 A1 | 7/1995 | | WO | WO 01/62164 A2 | 8/2001 |
| WO | WO 95/18383 A1 | 7/1995 | | WO | WO 01/62169 A2 | 8/2001 |
| WO | WO 95/18572 A1 | 7/1995 | | WO | WO 01/78605 A2 | 10/2001 |
| WO | WO 95/19739 A1 | 7/1995 | | WO | WO 01/91646 A1 | 12/2001 |
| WO | WO 95/20360 A1 | 8/1995 | | WO | WO 02/07608 A2 | 1/2002 |
| WO | WO 95/23557 A1 | 9/1995 | | WO | WO 02/07618 A1 | 1/2002 |
| WO | WO 95/24865 A1 | 9/1995 | | WO | WO 02/17799 A1 | 3/2002 |
| WO | WO 95/25471 A3 | 9/1995 | | WO | WO 02/19920 A1 | 3/2002 |
| WO | WO 95/26562 A1 | 10/1995 | | WO | WO 02/19932 A1 | 3/2002 |
| WO | WO 95/29639 A1 | 11/1995 | | WO | WO 02/30297 A2 | 4/2002 |
| WO | WO 96/04858 A1 | 2/1996 | | WO | WO 02/32322 A2 | 4/2002 |
| WO | WO 96/19151 A1 | 6/1996 | | WO | WO 02/36028 A1 | 5/2002 |
| WO | WO 96/19152 A1 | 6/1996 | | WO | WO 02/043571 A2 | 6/2002 |
| WO | WO 96/20652 A1 | 7/1996 | | WO | WO 02/058568 A1 | 8/2002 |
| WO | WO 96/21119 A1 | 7/1996 | | WO | WO 02/060328 A1 | 8/2002 |
| WO | WO 96/22055 A1 | 7/1996 | | WO | WO 02/067785 A2 | 9/2002 |
| WO | WO 96/23448 A1 | 8/1996 | | WO | WO 02/098302 A1 | 12/2002 |
| WO | WO 96/24301 A1 | 8/1996 | | WO | WO 03/000138 A2 | 1/2003 |
| WO | WO 96/27337 A1 | 9/1996 | | WO | WO 03/001329 A2 | 1/2003 |
| WO | WO 96/31155 A1 | 10/1996 | | WO | WO 03/013363 A1 | 2/2003 |
| WO | WO 96/35464 A1 | 11/1996 | | WO | WO 03/015604 A2 | 2/2003 |
| WO | WO 96/39085 A1 | 12/1996 | | WO | WO 03/020106 A2 | 3/2003 |
| WO | WO 96/39086 A1 | 12/1996 | | WO | WO 03/020139 A2 | 3/2003 |
| WO | WO 96/39087 A1 | 12/1996 | | WO | WO 03/024339 A1 | 3/2003 |
| WO | WO 96/39088 A1 | 12/1996 | | WO | WO 03/079909 A3 | 3/2003 |
| WO | WO 96/39089 A1 | 12/1996 | | WO | WO 03/030743 A2 | 4/2003 |
| WO | WO 97/00646 A1 | 1/1997 | | WO | WO 03/037193 A1 | 5/2003 |
| WO | WO 97/00647 A1 | 1/1997 | | WO | WO 03/047436 A3 | 6/2003 |
| WO | WO 97/06582 A1 | 2/1997 | | WO | WO 03/055402 A1 | 7/2003 |
| WO | WO 97/10763 A1 | 3/1997 | | WO | WO 03/057048 A1 | 7/2003 |
| WO | WO 97/10764 A1 | 3/1997 | | WO | WO 03/057058 A1 | 7/2003 |
| WO | WO 97/11648 A2 | 4/1997 | | WO | WO 03/063694 A1 | 8/2003 |
| WO | WO 97/11649 A1 | 4/1997 | | WO | WO 03/077769 A1 | 9/2003 |
| WO | WO 97/15237 A1 | 5/1997 | | WO | WO 03/079911 A1 | 10/2003 |
| WO | WO 97/24073 A1 | 7/1997 | | WO | WO 03/082126 A1 | 10/2003 |
| WO | WO 97/24993 A1 | 7/1997 | | WO | WO 03/088845 A2 | 10/2003 |
| WO | WO 97/30644 A1 | 8/1997 | | WO | WO 03/090630 A2 | 11/2003 |
| WO | WO 97/34533 A1 | 9/1997 | | WO | WO 03/094743 A1 | 11/2003 |
| WO | WO 97/37598 A1 | 10/1997 | | WO | WO 03/094745 A1 | 11/2003 |
| WO | WO 97/39688 A2 | 10/1997 | | WO | WO 03/094746 A1 | 11/2003 |
| WO | WO 98/17180 A1 | 4/1998 | | WO | WO 03/094747 A1 | 11/2003 |
| WO | WO 98/27880 A1 | 7/1998 | | WO | WO 03/101313 A1 | 12/2003 |
| WO | WO 98/30153 A1 | 7/1998 | | WO | WO 03/105698 A2 | 12/2003 |
| WO | WO 98/47436 A1 | 10/1998 | | WO | WO 03/105702 A2 | 12/2003 |
| WO | WO 99/03407 A1 | 1/1999 | | WO | WO 2004/006980 A2 | 1/2004 |
| WO | WO 99/03408 A1 | 1/1999 | | WO | WO 2004/019769 A1 | 3/2004 |
| WO | WO 99/03409 A1 | 1/1999 | | WO | WO 2004/021868 A2 | 3/2004 |
| WO | WO 99/12483 A1 | 3/1999 | | WO | WO 2004/028585 A2 | 4/2004 |
| WO | WO 99/12487 A1 | 3/1999 | | WO | WO 2004/032754 A2 | 4/2004 |
| WO | WO 99/12488 A1 | 3/1999 | | WO | WO 2004/032760 A2 | 4/2004 |
| WO | WO 99/15086 A1 | 4/1999 | | WO | WO 2004/032762 A1 | 4/2004 |
| WO | WO 99/15091 A1 | 4/1999 | | WO | WO 2004/032763 A2 | 4/2004 |
| WO | WO 99/23933 A2 | 5/1999 | | WO | WO 2004/034875 A2 | 4/2004 |
| WO | WO 99/23959 A1 | 5/1999 | | WO | WO 2004/047626 A1 | 6/2004 |
| WO | WO 99/25261 A1 | 5/1999 | | WO | WO 2004/047653 A2 | 6/2004 |
| WO | WO 99/29244 A1 | 6/1999 | | WO | WO 2004/049956 A2 | 6/2004 |
| WO | WO 99/34744 A1 | 7/1999 | | WO | WO 2004/052426 A2 | 6/2004 |
| WO | WO 99/45849 A1 | 9/1999 | | WO | WO 2004/056276 A1 | 7/2004 |
| WO | WO 99/48430 A1 | 9/1999 | | WO | WO 2004/056277 A1 | 7/2004 |
| WO | WO 99/51158 A1 | 10/1999 | | WO | WO 2004/062516 A1 | 7/2004 |
| WO | WO 00/24322 A1 | 5/2000 | | WO | WO 2004/078050 A2 | 9/2004 |
| WO | WO 00/24330 A1 | 5/2000 | | WO | WO 2004/078051 A2 | 9/2004 |
| WO | WO 00/41638 A1 | 7/2000 | | WO | WO 2004/086987 A1 | 10/2004 |
| WO | WO 00/48506 A1 | 8/2000 | | WO | WO 2004/096015 A2 | 11/2004 |
| WO | WO 00/53112 A2 | 9/2000 | | WO | WO 2004/096057 A2 | 11/2004 |
| WO | WO 00/54653 A1 | 9/2000 | | WO | WO 2004/103157 A2 | 12/2004 |
| WO | WO 00/57796 A1 | 10/2000 | | WO | WO 2004/105593 A2 | 12/2004 |
| WO | WO 00/64365 A1 | 11/2000 | | WO | WO 2004/105621 A1 | 12/2004 |
| WO | WO 00/72762 A1 | 12/2000 | | WO | WO 2004/112618 A2 | 12/2004 |
| WO | WO 00/72765 A1 | 12/2000 | | WO | WO 2004/112652 A2 | 12/2004 |
| WO | WO 01/03587 A1 | 1/2001 | | WO | WO 2005/027983 A2 | 3/2005 |
| WO | WO 01/05702 A1 | 1/2001 | | WO | WO 2005/037329 A2 | 4/2005 |
| WO | WO 01/10482 A1 | 2/2001 | | WO | WO 2005/044078 A2 | 5/2005 |
| WO | WO 01/35845 A1 | 5/2001 | | WO | WO 2005/055846 A1 | 6/2005 |
| WO | WO 01/54594 A1 | 8/2001 | | WO | WO 2005/072634 A2 | 8/2005 |
| WO | WO 01/58371 A1 | 8/2001 | | WO | WO 2005/078892 A1 | 8/2005 |
| WO | WO 01/62158 A2 | 8/2001 | | WO | WO 2005/096954 A2 | 10/2005 |
| WO | WO 01/62161 A1 | 8/2001 | | WO | WO 2005/112806 A2 | 12/2005 |
| WO | WO 01/62162 A1 | 8/2001 | | WO | WO 2005/112808 A1 | 12/2005 |

| | | | |
|---|---|---|---|
| WO | WO 2005/115251 A2 | 12/2005 |
| WO | WO 2005/117735 A1 | 12/2005 |
| WO | WO 2005/122936 A1 | 12/2005 |
| WO | WO 2006/027014 A1 | 3/2006 |
| WO | WO 2006/044490 A2 | 4/2006 |
| WO | WO 2006/044581 A2 | 4/2006 |
| WO | WO 2006/044810 A2 | 4/2006 |
| WO | WO 2006/051252 A1 | 5/2006 |
| WO | WO 2006/059067 A1 | 6/2006 |
| WO | WO 2006/083748 A1 | 8/2006 |
| WO | WO 2006/092563 A1 | 9/2006 |
| WO | WO 2006/092565 A1 | 9/2006 |
| WO | WO 2006/115958 A1 | 11/2006 |
| WO | WO 2006/125940 A1 | 11/2006 |
| WO | WO 2006/132992 A1 | 12/2006 |
| WO | WO 2007/002180 A2 | 1/2007 |
| WO | WO 2007/016290 A2 | 2/2007 |
| WO | WO 2007/018898 A2 | 2/2007 |
| WO | WO 2007/098220 A2 | 8/2007 |
| WO | WO 2007/121579 A1 | 11/2007 |
| WO | WO 2007/137304 A2 | 11/2007 |
| WO | WO 2007/139734 A2 | 12/2007 |
| WO | WO 2007/142625 A2 | 12/2007 |
| WO | WO 2008/021969 A2 | 2/2008 |
| WO | WO 2008/039270 A2 | 4/2008 |
| WO | WO 2008/045383 A2 | 4/2008 |
| WO | WO 2008/109125 A1 | 9/2008 |
| WO | WO 2010/063795 A1 | 6/2010 |

OTHER PUBLICATIONS

Disclosed Anonymously, "Motor-Driven Surgical Stapler Improvements," Research Disclosure Database No. 526041, Published: Feb. 2008.

European Search Report, Application 07252583.5, dated Oct. 5, 2007 (7 pages).

B.R. Coolman, DVM, MS et al., "Comparison of Skin Staples With Sutures for Anastomosis of the Small Intestine in Dogs," Abstract; http://www.blackwell-synergy.com/doi/abs/10.1053/jvet.2000.7539?cookieSet=1&journalCode=vsu which redirects to http://www3.interscience.wiley.com/journal/119040681/abstract?CRETRY=1&SRETRY=0; [online] accessed: Sep. 22, 2008 (2 pages).

The Sodem Aseptic Battery Transfer Kit, Sodem Systems, 2000, 3 pages.

"Biomedical Coatings," Fort Wayne Metals, Research Products Corporation, obtained online at www.fwmetals.com on Jun. 21, 2010 (1 page).

Van Meer et al., "A Disposable Plastic Compact Wrist for Smart Minimally Invasive Surgical Tools," LAAS/CNRS (Aug. 2005).

Breedveld at al., "A New, Easily Miniaturized Sterrable Endoscope," IEEE Engineering in Medicine and Biology Magazine (Nov./Dec. 2005).

D. Tuite, Ed., "Get the Lowdown on Ultracapacitors," Nov. 15, 2007; [online] URL: http://electronicdesign.com/Articles/Print.cfm?ArticleID=17465, accessed Jan. 15, 2008 (5 pages).

Datasheet for Panasonic TK Relays Ultra Low Profile 2 A Polarized Relay, Copyright Matsushita Electric Works, Ltd. (Known of at least as early as Aug. 17, 2010), 5 pages.

\* cited by examiner

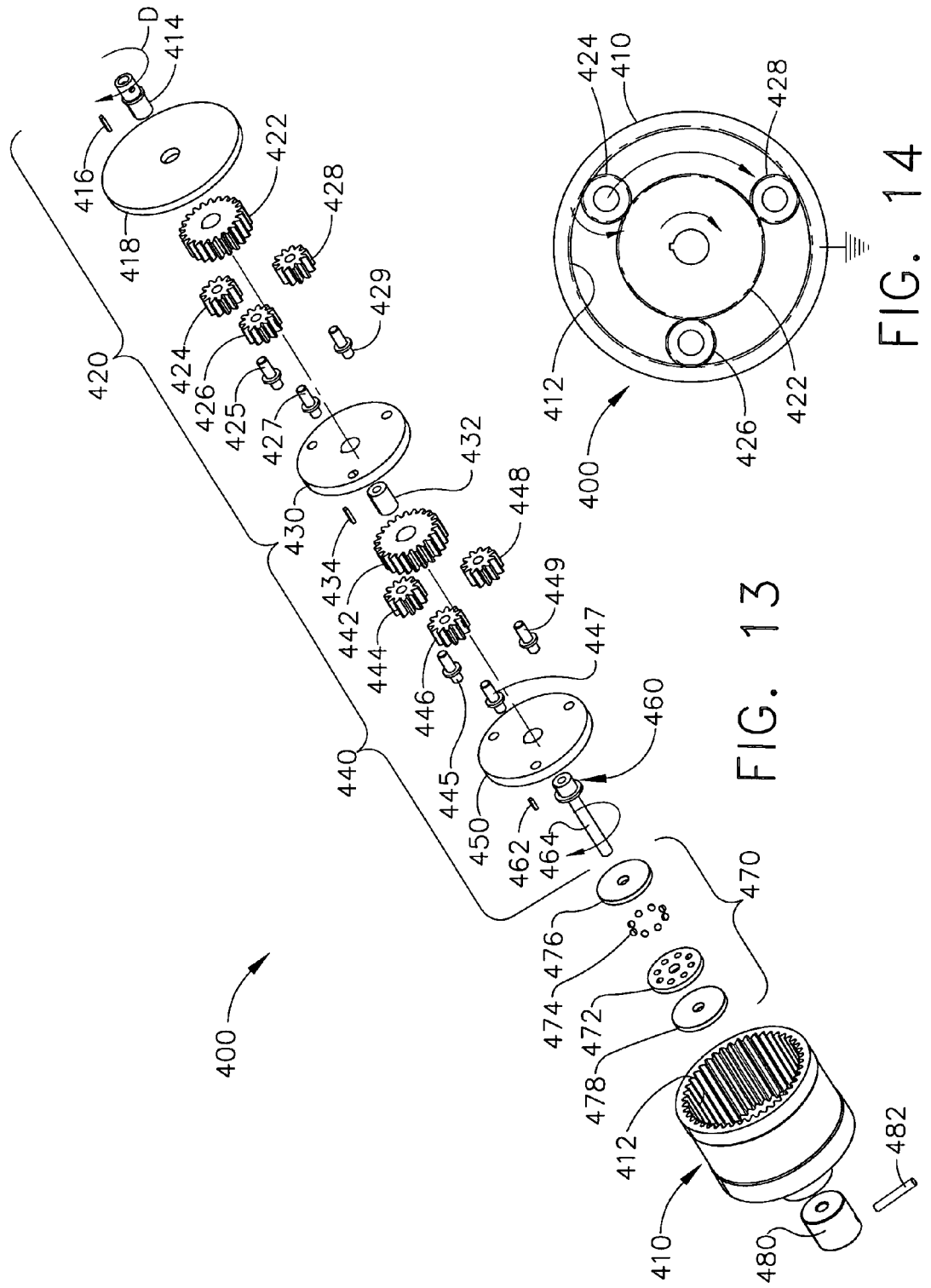

MANUALLY DRIVEN SURGICAL CUTTING AND FASTENING INSTRUMENT

BACKGROUND

The present invention generally concerns surgical instruments and, more particularly, surgical cutting and fastening instruments. The present invention may have application in conventional endoscopic and open surgical instrumentation as well as application in robotic-assisted surgery.

Surgical staplers have been used in the prior art to simultaneously make a longitudinal incision in tissue and apply lines of staples on opposing sides of the incision. Such instruments commonly include a pair of cooperating jaw members that, if the instrument is intended for endoscopic or laparoscopic applications, are capable of passing through a cannula passageway. One of the jaw members receives a staple cartridge having at least two laterally spaced rows of staples. The other jaw member defines an anvil having staple-forming pockets aligned with the rows of staples in the cartridge. The instrument includes a plurality of reciprocating wedges which, when driven distally, pass through openings in the staple cartridge and engage drivers supporting the staples to effect the firing of the staples toward the anvil.

Over the years, a variety of improvements have been made to such instruments. For example, some surgical staplers have been manufactured with electrically powered or pneumatically powered drive mechanisms. Such staplers, while extremely effective and easy to use, can be cost prohibitive for some users.

Consequently there is a need for a surgical stapling device that is effective and easy to use, yet more economical than other powered surgical stapling devices.

SUMMARY

In one general aspect, the present invention is directed to a surgical instrument that comprises a handle assembly that supports a closure drive that is configured to generate a closing motion and an opening motion. A firing drive is supported by the handle assembly and is configured to selectively generate a rotary firing motion and a rotary retraction motion upon manual actuation of a firing trigger that is operably coupled to the handle assembly. An elongate shaft assembly is coupled to the handle assembly and communicates with the closure drive and the firing drive to separately transfer the closing motion and the rotary firing motion. Various embodiments of the surgical instrument further comprises an end effector that is coupled to the elongate shaft assembly. The end effector comprises an elongate channel that is sized to receive a staple cartridge therein. An anvil is pivotally coupled to the elongate channel. The anvil is pivotally responsive to the open and closing motions from the elongate shaft assembly. A cutting and severing member is operably supported within the elongate channel and is responsive to the rotary firing and retraction motions from the elongate shaft assembly. In various embodiments, the elongate channel may be fabricated from metal utilizing conventional progressive die stamping techniques. Likewise, the anvil may be stamped from a piece of metal to reduce manufacturing costs.

In another general aspect, the present invention is directed to a method for processing an instrument for surgery. The method may comprise obtaining a surgical instrument of the type describe above, sterilizing it and thereafter storing it in a sterile container.

In another general aspect, the present invention is directed to a surgical stapling and severing apparatus that comprises a handle assembly that movably supports a closure shuttle therein. A closure trigger is operably supported by the handle assembly and is operable to apply a closing and opening force to the closure shuttle. An elongate spine assembly that has a distal end and a proximal end is oriented such that the proximal end is supported by the closure shuttle and the distal end is coupled to an elongate channel configured to receive a staple cartridge therein. An anvil is pivotally coupled to the elongate channel. A closure tube assembly is supported on the elongate spine assembly and is coupled to the handle assembly. The closure tube assembly cooperates with the anvil such that upon application of the closure force to the closure shuttle, the spine assembly moves distally within the closure tube assembly causing the anvil to pivot to a closed position and whereupon application of the opening force to the closure shuttle, the spine assembly moves proximally within the closure tube assembly causing the anvil to pivot to an open position. A cutting and severing member is operably supported within the elongate channel and a shifter assembly is supported in the handle assembly. The shifter assembly is selectively movable between a firing orientation and a retraction orientation. The shifter assembly cooperates with a firing trigger such that upon actuation of the firing trigger when the shifter assembly is in the firing orientation, the shifter assembly applies a rotary firing motion to the cutting and severing member to drive the cutting and severing member distally through the elongate channel and such that upon another actuation of the firing trigger when the shifter assembly is in the retraction orientation, the shifter assembly applies a rotary retraction motion to the cutting and severing member to drive the cutting and severing member proximally through the elongate channel.

DRAWINGS

Various embodiments of the present invention are described herein by way of example in conjunction with the following Figures, wherein like numerals may be used to describe like parts and wherein:

FIG. 13 is an isometric exploded assembly view of a planetary gear assembly embodiment of the present invention;

FIG. 14 is an end view of the planetary gear assembly of FIG. 13 with the cover plate removed therefrom;

DETAILED DESCRIPTION

Figure 1:
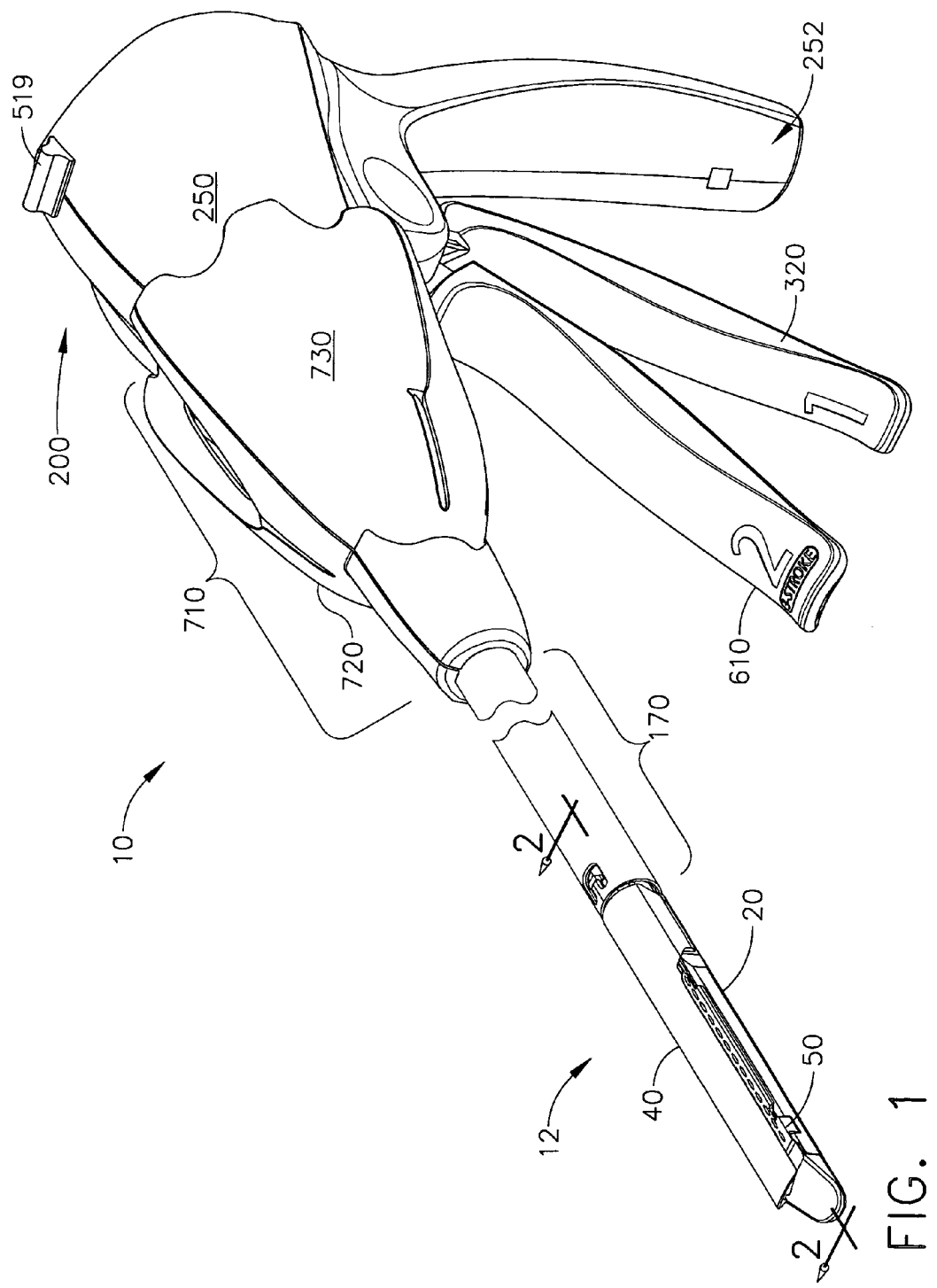
FIG. 1 is a perspective view of an embodiment of a surgical cutting and fastening instrument of the present invention.

Turning to the Drawings wherein like numerals denote like components throughout the several views, FIG. 1 depicts a surgical stapling and severing instrument 10 that is capable of practicing several unique benefits of the present invention. The surgical stapling and severing instrument 10 incorporates an end effector 12 that is manually actuated by manipulation of control members on a handle assembly 200 to which it is attached. A variety of different end effector constructions are known. One type of end effector 12 that may be employed with various embodiments of the present invention is depicted in FIGS. 1, 2, and 5-9. As can be seen in some of those Figures, the end effector 12 employs an E-beam firing mechanism ("knife bar") 30 that advantageously controls the spacing of the end effector 12. Various aspects of E-beam firing mechanisms are described in U.S. Pat. No. 6,978,921, entitled Surgical Stapling Instrument Incorporating an E-Beam Firing Mechanism to Shelton, IV. et al., the relevant portions of which are herein incorporated by reference. As the present Detailed Description proceeds, however, those of ordinary skill in the art will appreciate that other knife and firing bar configurations may be advantageously employed without departing form the spirit and scope of the present invention.

It will further be appreciated that the terms "proximal" and "distal" are used herein with reference to a clinician gripping a handle of an instrument. Thus, the end effector 12 is distal with respect to the more proximal handle assembly 200. It will also be understood that for convenience and clarity, spatial terms such as "vertical" and "horizontal" are used herein with respect to the drawings. However, surgical instruments are used in many orientations and positions, and these terms are not intended to be limiting and absolute.

Figure 2:
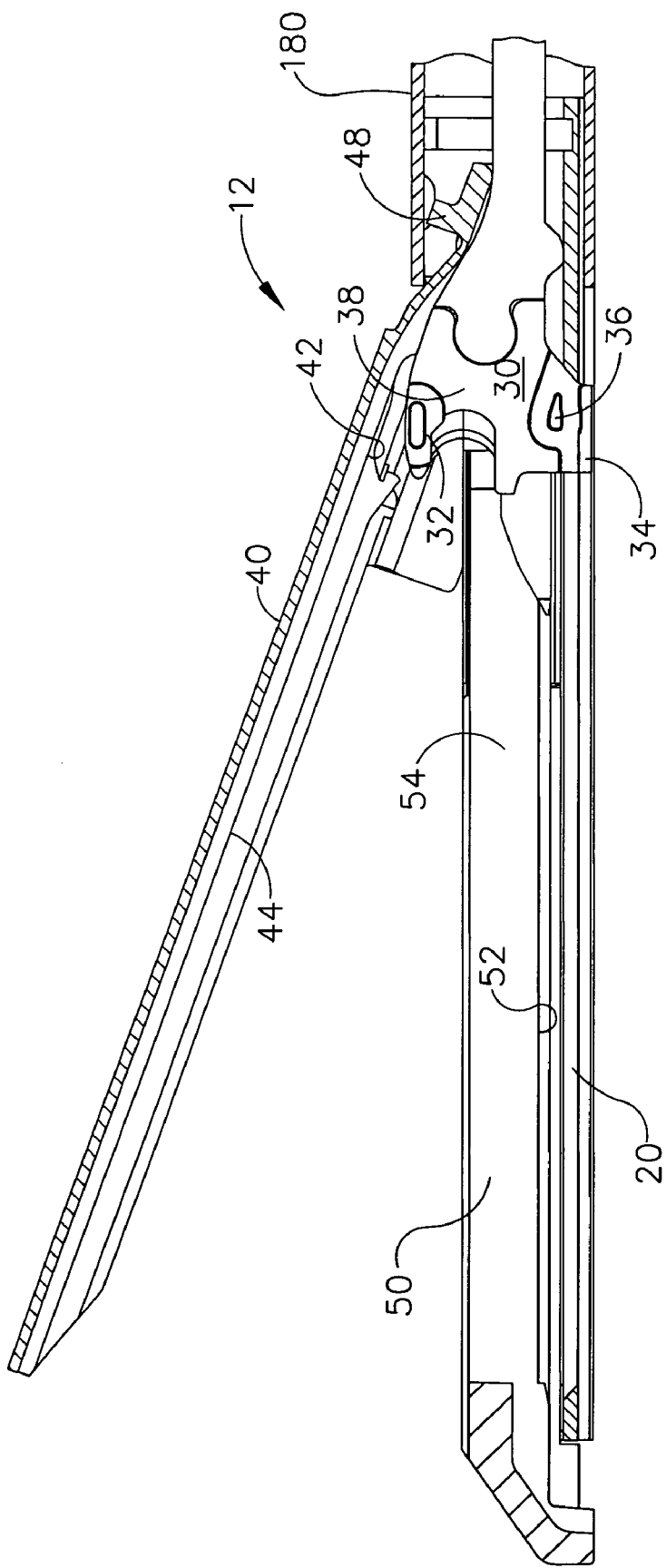
FIG. 2 is a cross-sectional side elevational view taken along the line 2-2 of FIG. 1 of an end effector embodiment of the present invention.
Figure 6:
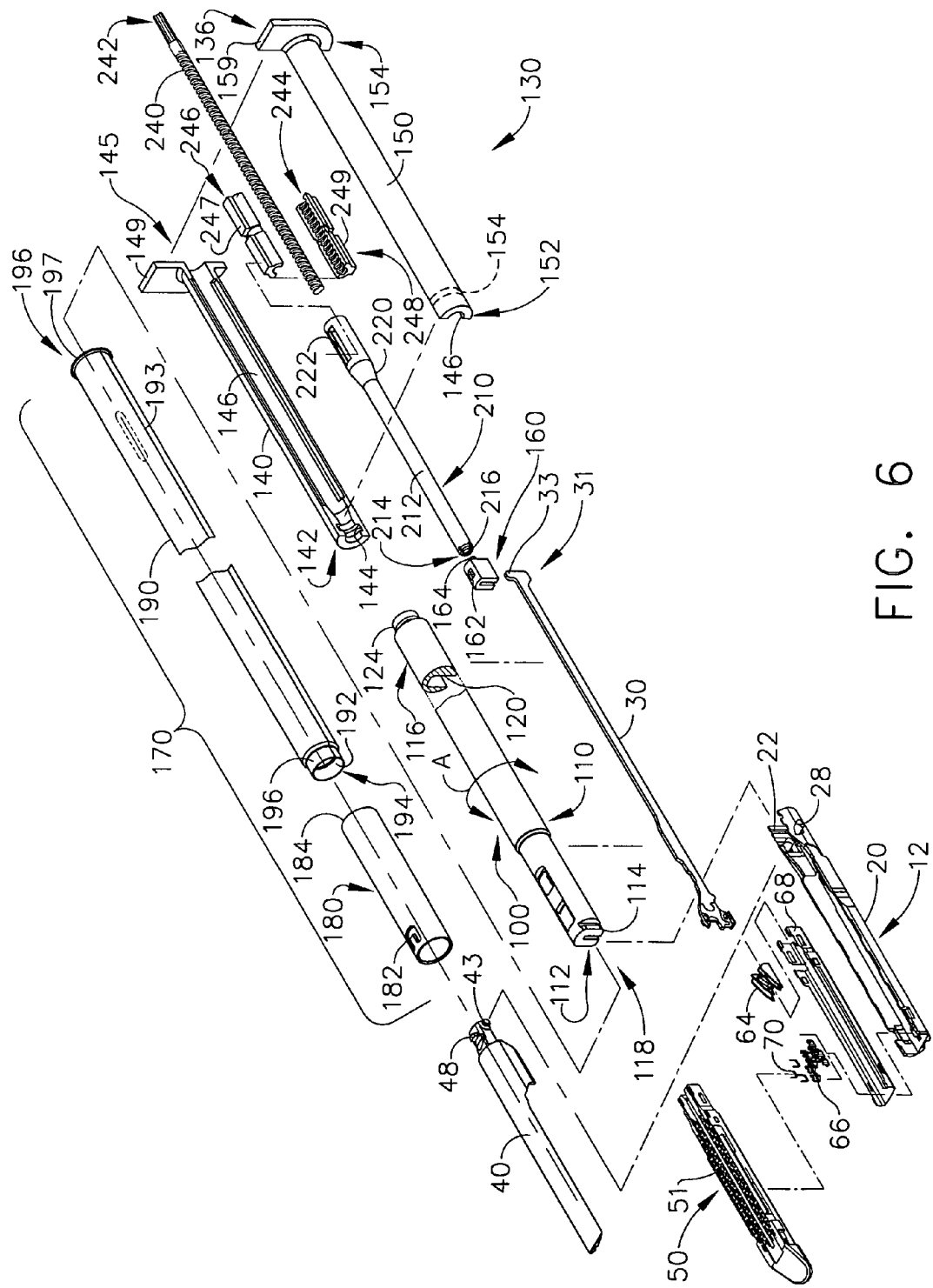
FIG. 6 is an isometric exploded view of the end effector or implement portion and spine assembly of various embodiments of the present invention.
Figure 7:
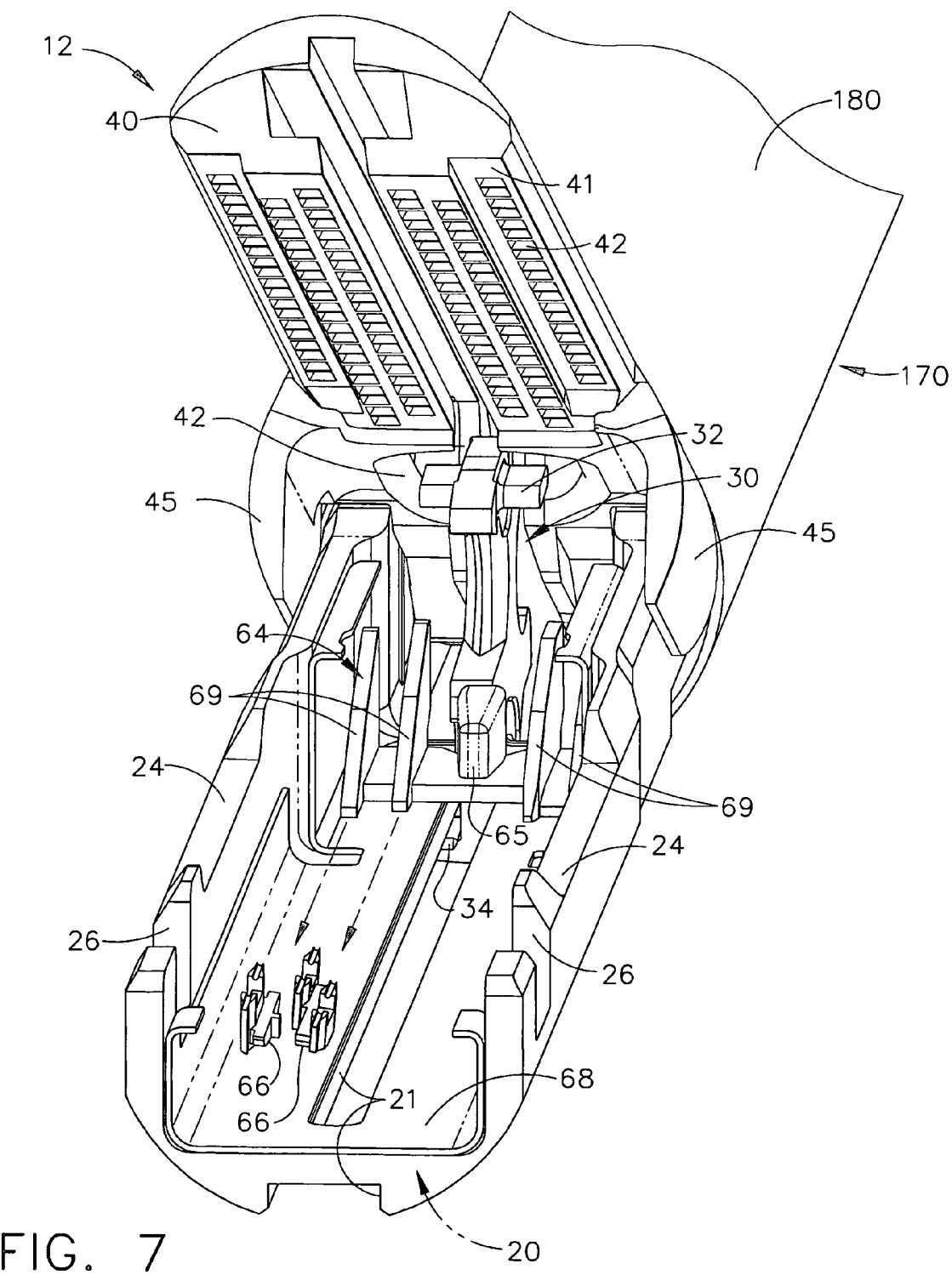
FIG. 7 is an isometric view of the end effector of FIG. 2 with the anvil in the open position and the staple cartridge largely removed exposing a single staple driver and double staple driver and the wedge sled in its start position against a middle pin of the knife bar.

As can be seen in FIGS. 2, 6, and 7, the end effector 12 includes an elongate channel 20 that has a pivotally translatable anvil 40 attached thereto. In one embodiment, the channel 20 may be fabricated from metal utilizing conventional progressive die techniques and may be provided with corresponding openings for receiving the knife bar 30 therein. Such manufacturing methods may result in manufacturing costs that are lower than those conventional methods that are otherwise commonly employed to manufacture the elongate channels.

The elongate channel 20 is configured to receive and support a staple cartridge 50 that is responsive to the knife bar 30 to drive staples 70 into forming contact with the anvil 40. It will be appreciated that, although a readily replaceable staple cartridge is advantageously described herein, a staple cartridge consistent with aspects of the present invention may be permanently affixed or integral to the elongate channel 20.

Figure 3:
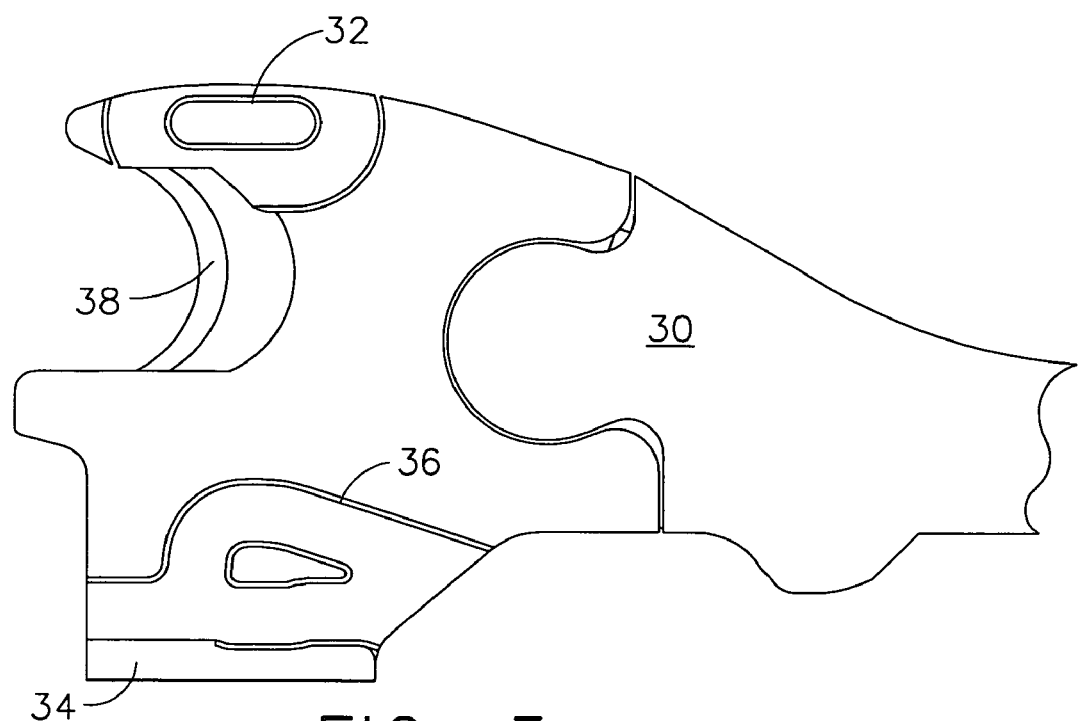
FIG. 3 is an enlarged side elevational view of a portion of a knife bar of the end effector embodiment of FIG. 2.
Figure 4:
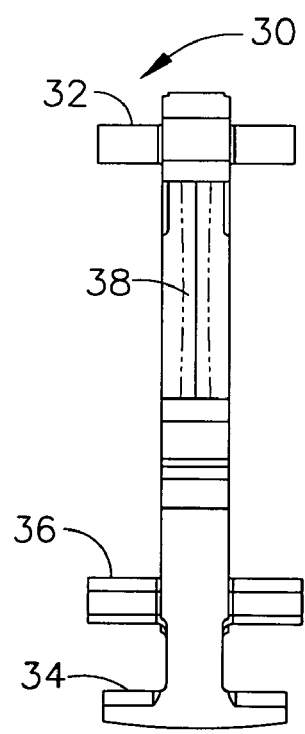
FIG. 4 is an enlarged front view of the knife bar of the end effector of FIG. 3.

With particular reference to FIGS. 2-4, in various embodiments, the knife bar 30 includes three vertically spaced pins that control the spacing of the end effector 12 during firing. In particular, an upper pin 32 is staged to enter an anvil pocket 42 near the pivot between the anvil 40 and elongate channel 20. When fired with the anvil 40 closed, the upper pin 32 advances distally within a longitudinal anvil slot 44 extending distally through anvil 40. Any minor upward deflection in the anvil 40 is overcome by a downward force imparted by the upper pin 32.

Knife bar 30 also includes a lower most pin 34, or knife bar cap, that upwardly engages a channel slot 23 formed in the elongate channel 20, thereby cooperating with the upper pin 32 to draw the anvil 40 and the elongate channel 20 slightly closer together in the event of excess tissue clamped therebetween. In various embodiments, the knife bar 30 may advantageously include a middle pin 36 that passes through a firing drive slot 52 formed in a lower surface of the cartridge 50 and an upward surface of the elongate channel 20, thereby driving the staples 70 therein as described below. The middle pin 36, by sliding against the elongate channel 20, advantageously resists any tendency for the end effector 12 to be pinched shut at its distal end. However, the unique and novel aspects of various embodiments of the present invention may be attained through use of other knife bar arrangements.

Returning to FIGS. 2-4, a distally presented cutting edge 38 between the upper and middle pins 32, 36 on the knife bar 30 traverses through a proximally presented, vertical slot 54 in the cartridge 50 to sever clamped tissue. The affirmative positioning of the knife bar 30 with regard to the elongate channel 20 and anvil 40 assure that an effective cut is performed.

The end effector 12 of the surgical stapling and severing instrument is depicted in further detail in FIGS. 5-10. As will be described in further detail below, manipulation of various control members on the handle assembly 200 produces separate and distinct closing and firing motions that actuate the end effector 12. The end effector 12 advantageously maintains the clinical flexibility of this separate and distinct closing and firing (i.e., stapling and severing).

Figure 5:
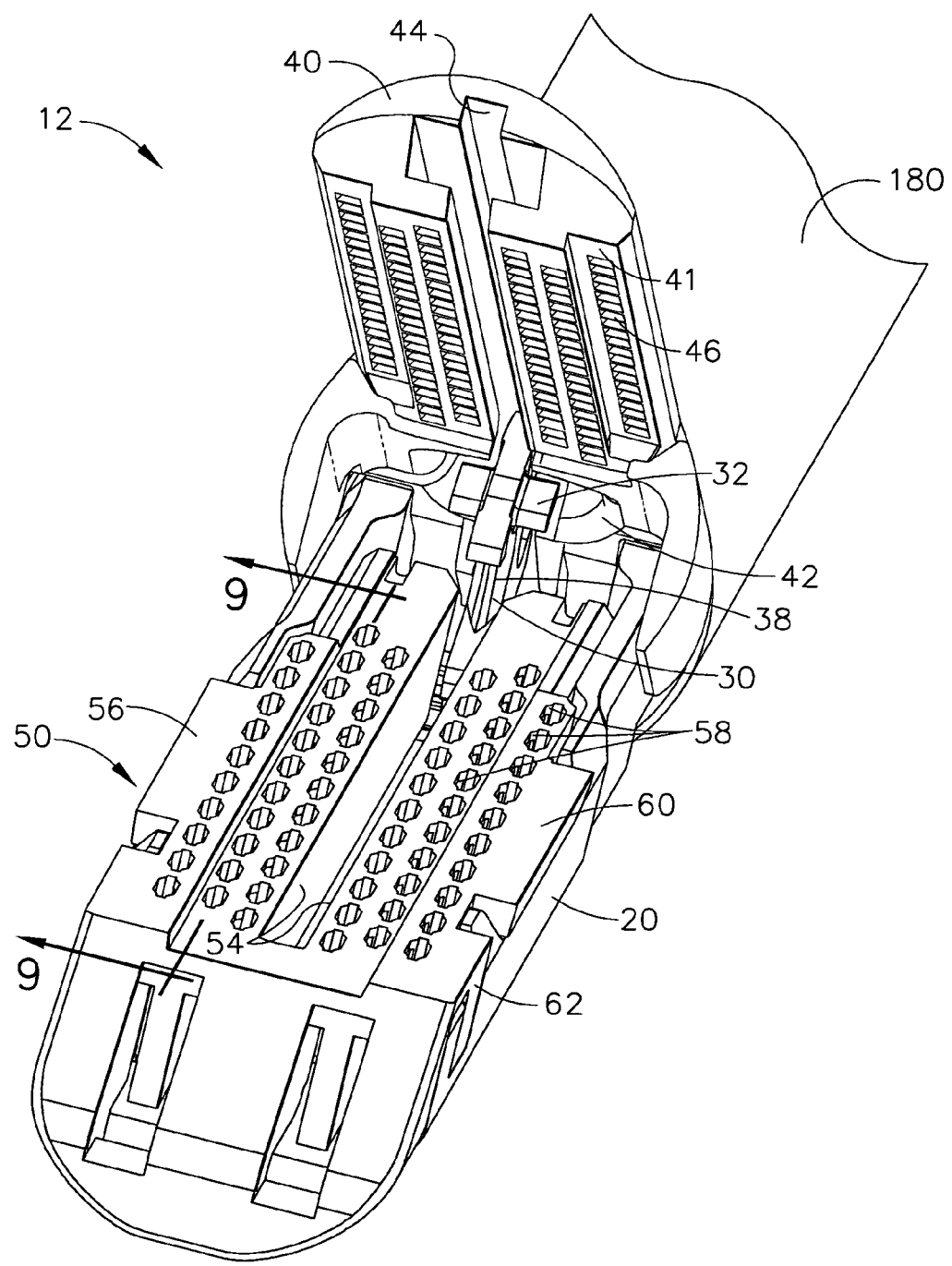
FIG. 5 is an isometric view of the end effector of FIG. 2 at the distal end of the surgical cutting and fastening instrument of various embodiments of the present invention with the anvil in the open position.

FIG. 5 depicts the end effector 12, which is in an open position by a retracted spine assembly 100 (FIG. 6), with a staple cartridge 50 installed in the elongate channel 20. On a lower surface 41 of the anvil 40, a plurality of stapling forming pockets 46 are arrayed to correspond to a plurality of staple apertures 58 in an upper surface 56 of the staple cartridge 50. The knife bar 30 is at its proximal position, with the upper pin 32 aligned in a non-interfering fashion with the anvil pocket 42. The anvil pocket 42 is shown as communicating with the longitudinal anvil slot 44 in the anvil 40. The distally presented cutting edge 38 of the knife bar 30 is aligned with and proximally removed from the vertical slot 54 in the staple cartridge 50, thereby allowing removal of a spent cartridge 50 and insertion of an unfired cartridge 50, which is snapfit into the elongate channel 20. Specifically, extension features 60, 62 of the staple cartridge 50 engage recesses 24, 26, respectively (shown in FIG. 7) of the elongate channel 20.

FIG. 6 shows an embodiment of an implement portion 12 of the surgical stapling and severing instrument 10 in disassembled form. The staple cartridge 50 is shown as being comprised of a cartridge body 51, a wedge sled 64, single and double drivers 66, staples 70, and a cartridge tray 68. When assembled, the cartridge tray 68 holds the wedge sled 64, single and double drivers 66, and staples 70 inside the cartridge body 51.

The elongate channel 20 is coupled to the handle assembly 200 by means of a spine assembly 100 that includes a distal spine section 110 and a proximal spine section 130. The elongate channel 20 has proximally placed attachment cavities 22 that each receive a corresponding channel anchoring member 114 formed on the distal end 112 of the distal spine section 110. The elongate channel 20 also has anvil cam slots 28 that pivotally receive a corresponding anvil pivot 43 on the anvil 40. A closure sleeve assembly 170 is received over the spine assembly 100 and includes distal closure tube segment 180 and a proximal closure tube segment 190. See FIG. 6. The distal closure tube segment 180 includes a distally presented tab 182 that engages an anvil closure tab 48 proximate but distal to the anvil pivots 43 on the anvil 40 to thereby effect opening and closing of the anvil 40 by axially moving the spine assembly 100 within the closure tube assembly 170 as will be discussed in further detail below.

With particular reference to FIG. 7, a portion of the staple cartridge 50 is removed to expose portions of the elongate channel 20, such as recesses 24, 26 and to expose some components of the staple cartridge 50 in their unfired position. In particular, the cartridge body 51 (shown in FIG. 6) has been removed. The wedge sled 64 is shown at its proximal, unfired position with a pusher block 65 contacting the middle pin 36 (not shown in FIG. 7) of the knife bar 30. The wedge sled 64 is in longitudinal sliding contact upon the cartridge tray 68 and includes wedges 69 that force upward the single and double drivers 66 as the wedge sled 64 moves distally. Staples 70 (not shown in FIG. 7) resting upon the drivers 66 are also forced upward into contact with the staple forming pockets 42 on the anvil 40 to form closed staples. Also depicted is the channel slot 21 in the elongate channel 20 that is aligned with the vertical slot 54 in the staple cartridge 50.

Figure 8:
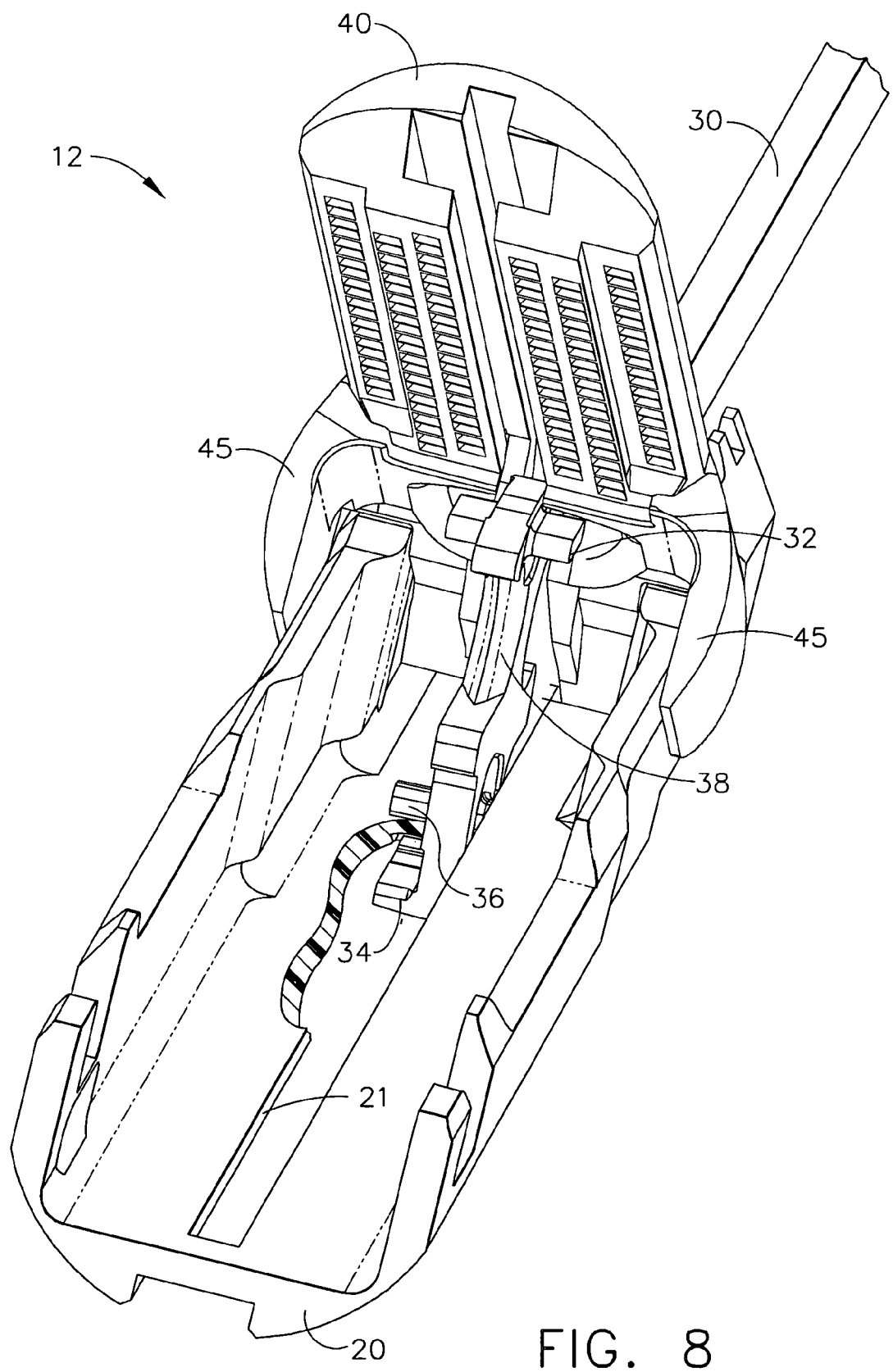
FIG. 8 is an isometric view of the end effector of FIG. 2 with the anvil in the open position and the staple cartridge completely removed and a portion of the elongate channel removed to expose the lowermost pin of the knife bar.

FIG. 8 depicts the end effector 12 of FIG. 7 with all of the staple cartridge 50 removed to show the middle pin 36 of the knife bar 30 as well as portion of the elongate channel 20 removed adjacent to the channel slot 21 to expose the lower pin or knife bar cap 34. Projecting downward from the anvil 40 near the pivot, a pair of opposing tissue stops 45 prevent tissue from being positioned too far up into the end effector 12 during clamping.

Figure 20:
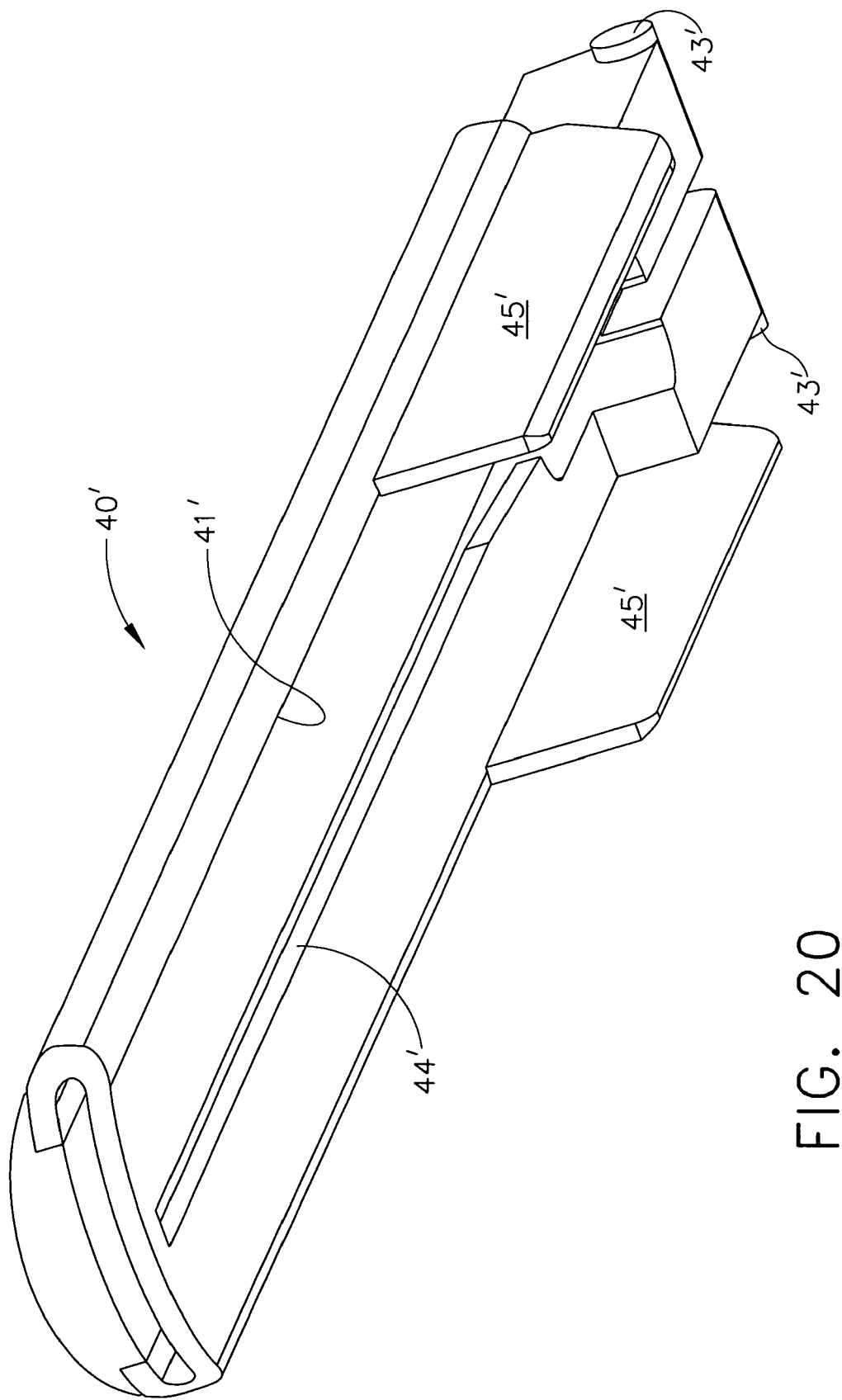
FIG. 20 is an isometric view of an alternative anvil embodiment of the present invention.

In other embodiments of the present invention, the anvil employed may comprise an anvil 40' that is stamped or otherwise formed out of metal or other suitable material as illustrated in FIG. 20 to reduce manufacturing costs. As can be seen in that Figure, the anvil 40' may be provided with a slot 44' for accommodating movement of a firing bar therethrough and also be formed with anvil pivots 43' and a closure tab (not shown) to facilitate its operation in the manner described above with respect to anvil 40. In this embodiment, the lower surface 41' of the anvil is not provided with staple forming pockets. The staples simply close as they come into contact with the hard lower surface 41'. Also, the embodiment depicted in FIG. 20 is formed with tissue stops 45'. Those of ordinary skill in the art will understand, however, that the anvil 40' may be formed with or without staple forming pockets and tissue stops if so desired. In addition, other variations of stamped anvils may be employed without departing from the spirit and scope of the present invention.

Figure 9:
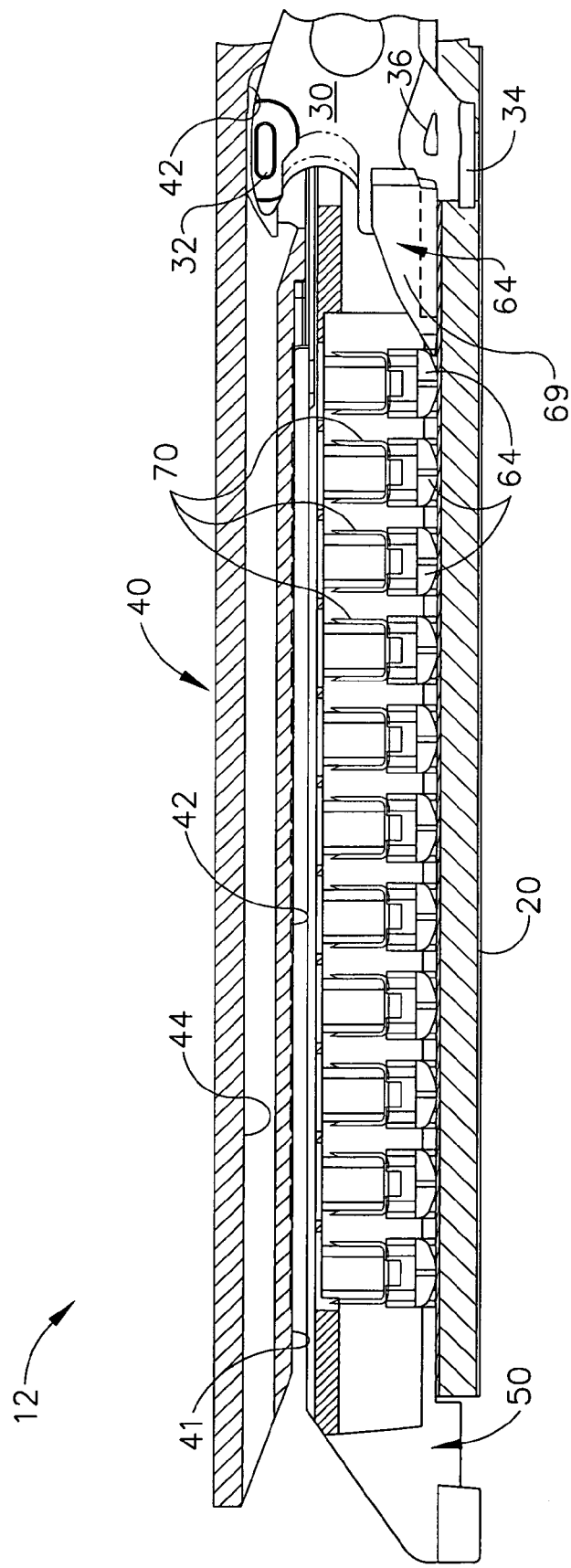
FIG. 9 is a side elevational view in cross-section showing a mechanical relationship between the anvil, elongate channel, and staple cartridge in the closed position of the surgical cutting and fastening instrument of FIG. 1, the section generally taken along lines 9-9 in FIG. 5 to expose the wedge sled, staple drivers, staples, but also depicting the knife bar along a longitudinal centerline.

FIG. 9 depicts the end effector 12 closed in a tissue clamping position with the knife bar 30 unfired. The upper pin 32 is in the anvil pocket 42, vertically aligned with the anvil slot 44 for distal longitudinal movement of the knife bar 30 during firing. The middle pin 36 is positioned to push the wedge sled 64 distally so that wedges 69 sequentially contact and lift double drivers 66 and the respective staples 70 into forming contact with staple forming pockets 42 in the lower surface 41 of the anvil 40.

As indicated above, the channel 20 is coupled to the handle assembly 200 by a spine assembly 100 that, in various embodiments, consists of a distal spine section 110 and a proximal spine section 130. As can be seen in FIG. 6, the distal spine section 110 has a distal end 114 that is attached to the elongate channel 20 and a proximal end 116 that is attached to a distal end 132 of the proximal spine section 130. The knife bar 30 is slidably received in a distal slot 118 in the distal end of the distal spine segment 110. A proximal end 31 of the knife bar 30 has an upstanding connector tab 33 formed thereon that is adapted to be received in a slot 162 in a connector block 160. The connector block 160 is attached to a firing rod 210 that is slidably supported within the proximal spine section 130. The connector block 160 is sized to be slidably received within a proximal slot 120 in the distal spine section 110.

The firing rod 210 may be fabricated from a polymer or other suitable material and be configured with a hollow shaft portion 212 that is sized to permit it to axially travel within the proximal slot 120 in the distal spine section 110. The firing rod 210 further has a proximal connector portion 220 that is sized to axially travel within an axial passage in the proximal spine section 130 as will be discussed in further detail below. The connector block 160 has a connector tab 164 protruding therefrom that is sized to be frictionally inserted into the tapered end 214 of the hollow shaft portion 212 of the firing rod 210. The tapered end 214 may have a series of slits 216 provided around its circumference to enable the protruding connector tab 164 on the connector block 160 to be inserted into the tapered end 214 and be frictionally attached thereto.

As can also be seen in FIG. 6, the proximal spine section 130 may be fabricated in two pieces to facilitate easy installation of the firing rod 210 therein and attachment to the distal spine section 110. More specifically, the proximal spine section 130 may comprise a right proximal spine segment 140 and a left proximal spine segment 150. The right proximal spine segment 140 has a right axial passage portion 146 that cooperates with a left axial passage portion 156 in the left proximal spine segment 150 to form an axial passage 132 in the proximal spine section 130 that is sized to axially and movably support the connector portion 220 of the firing rod 210 therein. In addition, the distal end 142 of the right spine segment 140 has a groove 144 therein that cooperates with a groove 154 in the distal end 152 of the left spine segment 150 to form an annular retention groove (not shown) in the proximal spine segment 130 for rotatably receiving a connection tab 124 protruding from the distal end 132 of the proximal spine section 130. Such arrangement permits the distal spine section 110 to be rotated relative to the proximal spine section 130. See arrow "A" in FIG. 6.

In various embodiments, the filing rod 210 is axially movable within the proximal spine section 130 by a firing screw 240, the operation of which will be discussed in further detail below. The firing screw 240 is coupled to the firing rod 210 by a bifurcated firing nut 244 that comprises nut segments 246 and 248. Nut segment 246 has an upstanding tab 247 protruding therefrom that is sized to protrude through a slot 222 in the connection portion 220 of the firing rod 210. Likewise, the nut segment 248 has an upstanding tab 249 that is sized to protrude through a slot (not shown) in the connection portion 220 of the firing rod 210. The portion of the tabs 247, 249 that protrude outward from the connection portion 220 are received in axial slots formed in the proximal spine segments 140, 150. Such tabs 247, 249 and slots, serve to facilitate axial travel of the firing rod 210 within the proximal spine segment 140 without permitting rotation of the firing rod 210 relative to the proximal spine segment 130.

Journaled on the spine assembly 100 is the closure tube assembly 170. See FIG. 6. The closure tube assembly 170 comprises a distal closure tube segment 180 and a proximal closure tube segment 190. The distal closure tube segment 180 and the proximal closure tube segment 190 may be fabricated from a polymer or other suitable material. The proximal closure tube segment 190 is hollow having an axial passage 192 extending therethrough that is sized to receive the spine assembly 100 therein. An axially extending slit 193 may be provided in the proximal closure tube 190 to facilitate easy installation of the spine assembly 100 therein. The distal end 194 of the proximal closure tube segment 190 may be provided with an extension 196 over which the proximal end 184 of the hollow distal closure tube segment 180 is inserted. The two closure tube segments 180, 190 may then be attached together with an appropriate adhesive material. The proximal end 196 of the proximal closure tube segment may be provided with a flange 197, the purpose of which will be discussed below.

Figure 10:
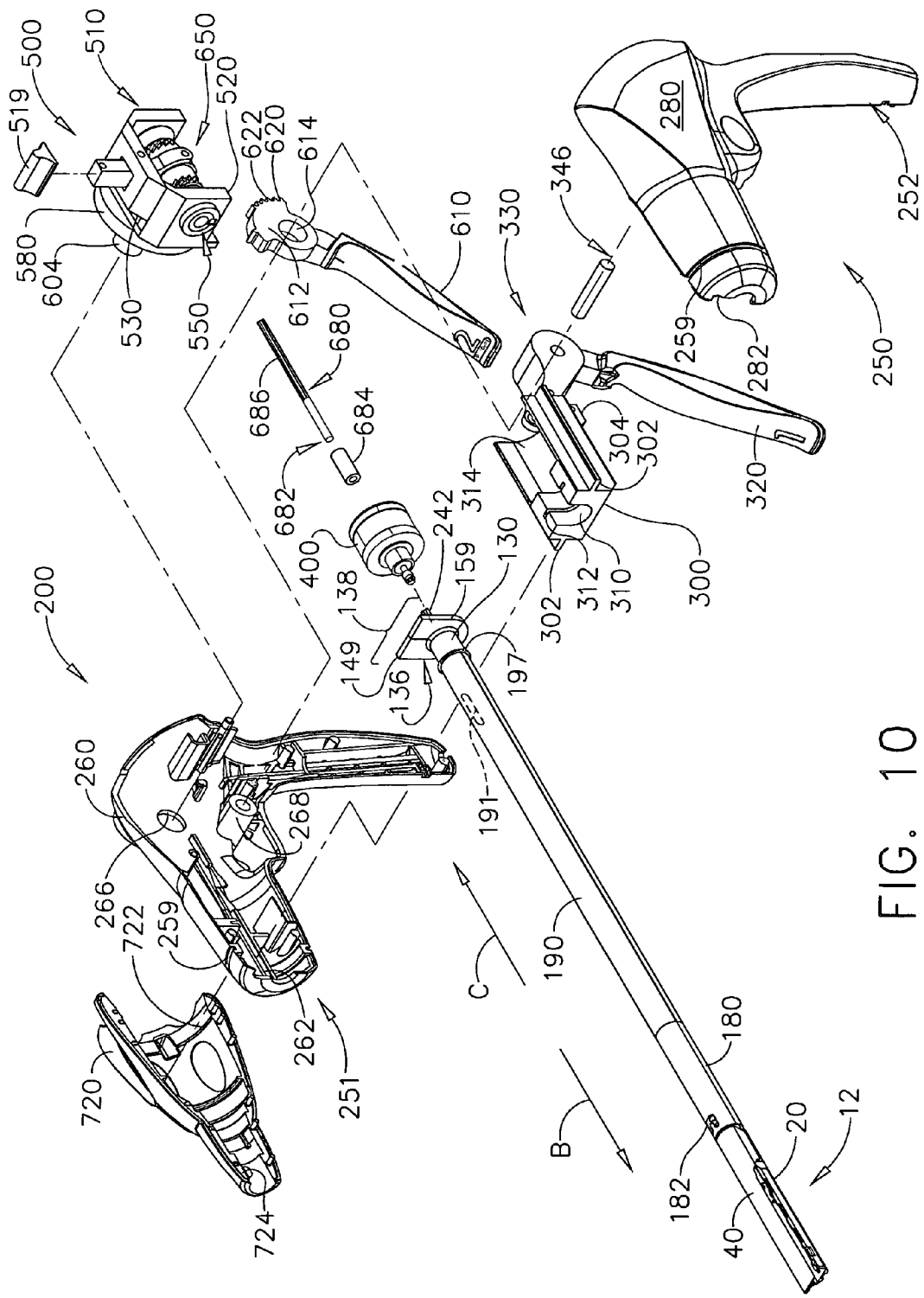
FIG. 10 is an isometric exploded assembly view of a surgical cutting and fastening instrument embodiment of the present invention.

FIG. 10 illustrates an exploded view of the handle assembly 200 and the components housed therein of various embodiments of the present invention for controlling the movement of the spine assembly 100 and the knife bar 30. As can be seen in that Figure, the handle assembly 200 comprises a pistol grip-type housing 250 that is fabricated in two pieces. For example, the housing 250 may comprise a right hand case member 260 and a left hand case member 280 that are molded or otherwise fabricated from a polymer material and are designed to mate together. Such case members 260 and 280 may be attached together by snap features, pegs and sockets molded or otherwise formed therein and/or by adhesive, screws, etc.

Supported within the housing 250 is a closure shuttle 300 that is coupled to a closure trigger 320 by a linkage assembly 330. Closure shuttle 300 may be configured as shown in FIG. 10 with a distal cradle portion 310 and a proximal cradle portion 314. The distal cradle portion 310 is configured to cradle the proximal end 136 of the proximal spine segment 130 therein. A base flange 138 is formed on the proximal end 136 of the proximal spine segment 130 and is received within a slot 312 in the closure shuttle 300. The base flange 138 is formed by a right side flange segment 149 formed on the proximal end 145 of the right proximal spine segment 140 and a left side flange segment 159 formed on the proximal end 154 of the left proximal spine segment 150. See FIG. 6.

As can be seen in FIG. 10, the closure shuttle 300 is provided with laterally extending rails 302 that are configured to be slidably received within rail guides 262 and 282 in the right hand case member 260 and left hand case member 280, respectively. Such arrangement permits the closure shuttle 300 to move axially in a distal direction (arrow "B") and a proximal direction (arrow "C") within the handle housing 250. Axial movement of the closure shuttle 300 (and the spine assembly 100) in the distal direction is created by moving the closure trigger 320 toward the pistol grip portion 252 of the handle housing 250 and axial movement of the closure shuttle 300 in the proximal direction (arrow "C") is created by moving the closure trigger 320 away from the pistol grip portion 252.

In various embodiments, the closure shuttle 300 is provided with a connector tab 304 that facilitates the attachment of the closure linkage assembly 330 thereto. See FIGS. 10-12. The closure linkage assembly 330 includes a closure arm 340 and a closure link 350. The closure arm 340 is pivotally pinned within the housing 250 by a closure pin 344 that extends through a first pivot hole 342 in the closure arm 340. The ends of the closure pin 344 are received in sockets 264 formed in the right hand case member 260 and left hand case member 280. Such arrangement permits the closure arm 340 to pivot about a first closure axis 346. See FIG. 10. The distal end 341 of the closure arm 340 is pinned to a proximal end 351 of the closure link 350 such that the proximal end 351 of the closure link 350 can pivot relative to the distal end 341 of the closure arm 340 about a proximal pivot axis 355. Likewise, the distal end 352 of the closure link 350 is pinned to the connection tab 304 on the closure shuttle 300 such that the distal end 355 can pivot relative to the connection tab 304 about a distal pivot axis 357. See FIG. 11.

Figure 11:
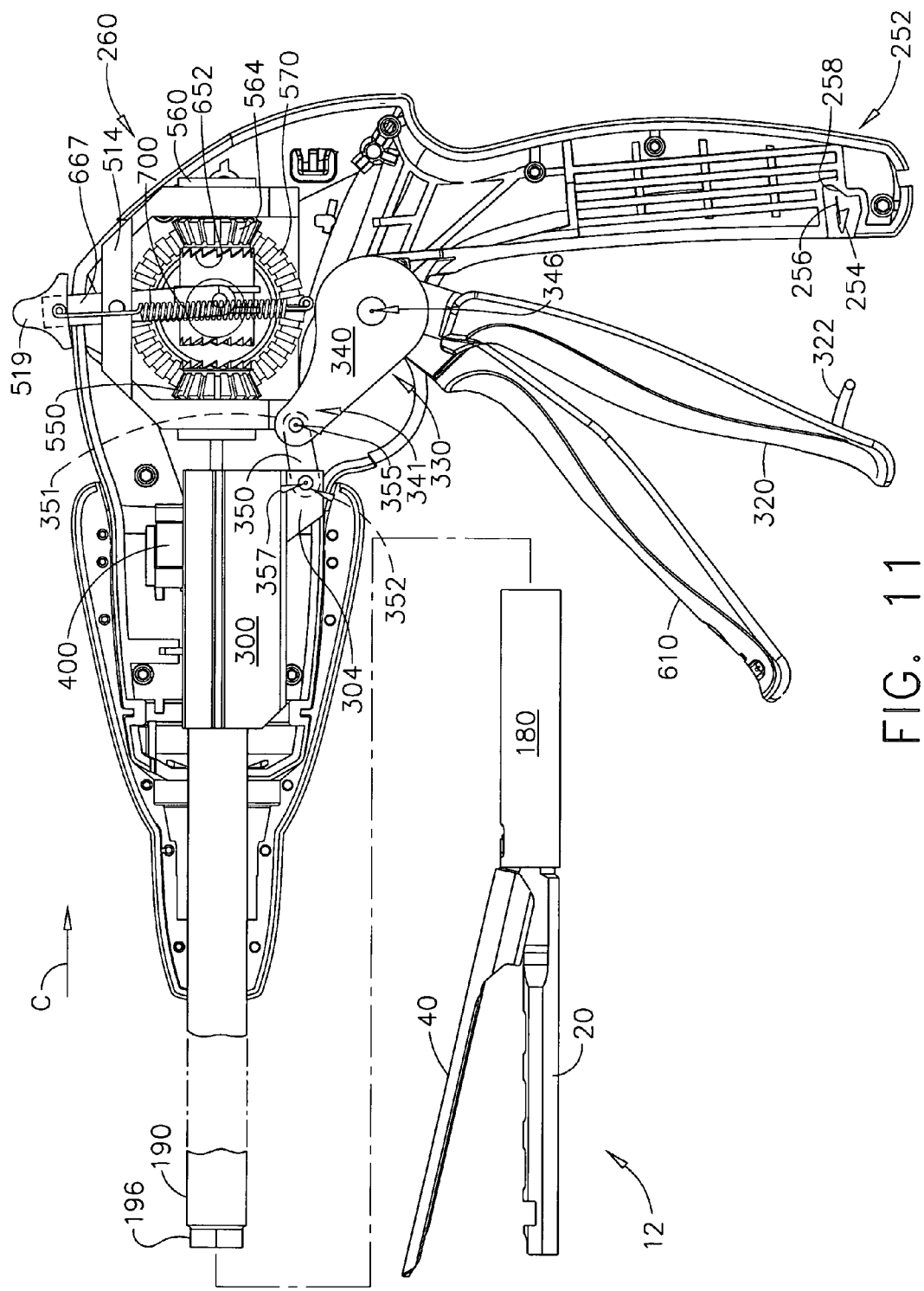
FIG. 11 is a side elevational view of the surgical cutting and fastening instrument of the present invention with the anvil in the open position and the handle assembly shown in cross-section to illustrate the positions of the various components housed therein.

FIG. 11 illustrates the end effector 12 in an open (unclamped) position. As can be seen in that Figure, the closure trigger 320 is pivoted away from the pistol grip portion 252 and the closure shuttle 300 is in its proximal position. When the closure shuttle 300 is in the proximal position, it draws the spine assembly 100 in the proximal "C" direction within the closure tube assembly 170. Such axial movement of the spine assembly 100 within the closure tube assembly 170 causes the closure tab 48 on the anvil to engage tab 182 on the distal closure tube segment 180 in such a manner as to cause the anvil 40 to pivot to the open position.

Figure 12:
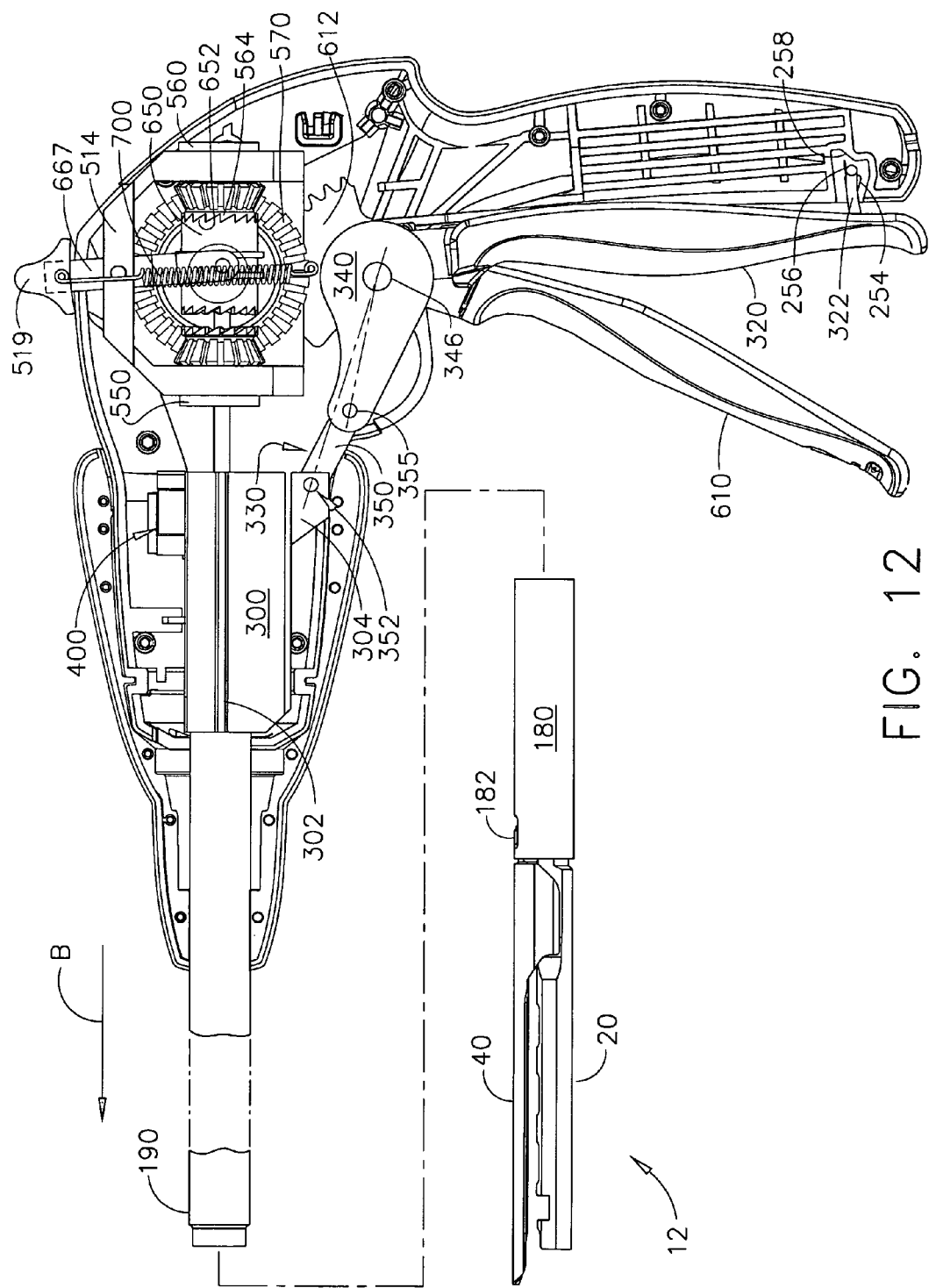
FIG. 12 is a side elevational view of the surgical cutting and fastening instrument of the present invention with the anvil in the closed position and the handle assembly shown in cross-section to illustrate the positions of the various components housed therein.

When the clinician desires to close the anvil 40 and to clamp tissue within the end effector 12, the clinician draws the closure trigger 320 toward the pistol grip 252 as shown in FIG. 12. As the clinician draws the closure trigger 320 toward the pistol grip 252, the closure linkage assembly 330 moves the closure shuttle 300 in the distal "B" direction until the closure linkage assembly 330 moves into the locked position illustrated in FIG. 12. When in that position, the linkage assembly 330 will tend to retain the closure shuttle 300 in that locked position. As the closure shuttle 300 is moved to the locked position, the spine assembly 100 is moved proximally within the closure tube assembly 170 causing the closure tab 48 on the anvil to contact the tab 182 on the distal closure tube segment 180 to thereby pivot the anvil 40 to the closed (clamped) position.

In various embodiments, to further retain the closure shuttle 300 in the closed position, the closure trigger 320 may be provided with a releasable locking mechanism that is adapted to engage the pistol grip 252 and releasably retain the closure trigger in the locked position. Other locking devices may also be used to releasably retain the closure shuttle 300 in the locked position. In the embodiment depicted in FIGS. 11 and 12, a lock member 322 in the form of a piece of spring steel or other flexible material is attached to the closure trigger 320. The free end of the lock member 322 is situated to enter into a retention pocket 254 in the pistol grip portion 252 of the handle 250. The lock member 322 frictionally engages the retention pocket 254 and retains the closure trigger 320 in the closed position.

Figure 16:
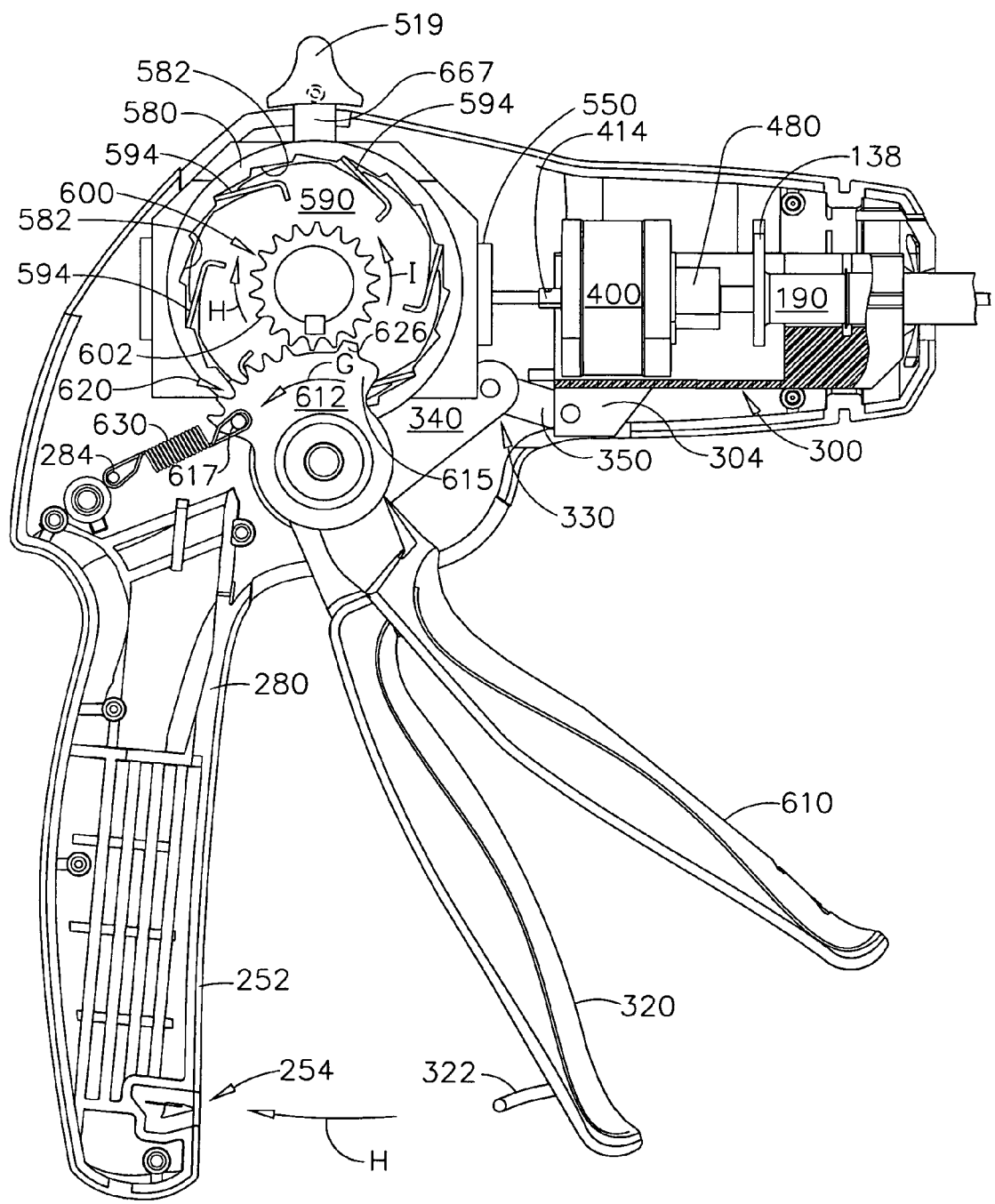
FIG. 16 is a cross-sectional view of a handle assembly embodiment of the present invention in a starting position wherein the anvil is in the open position.
Figure 18:
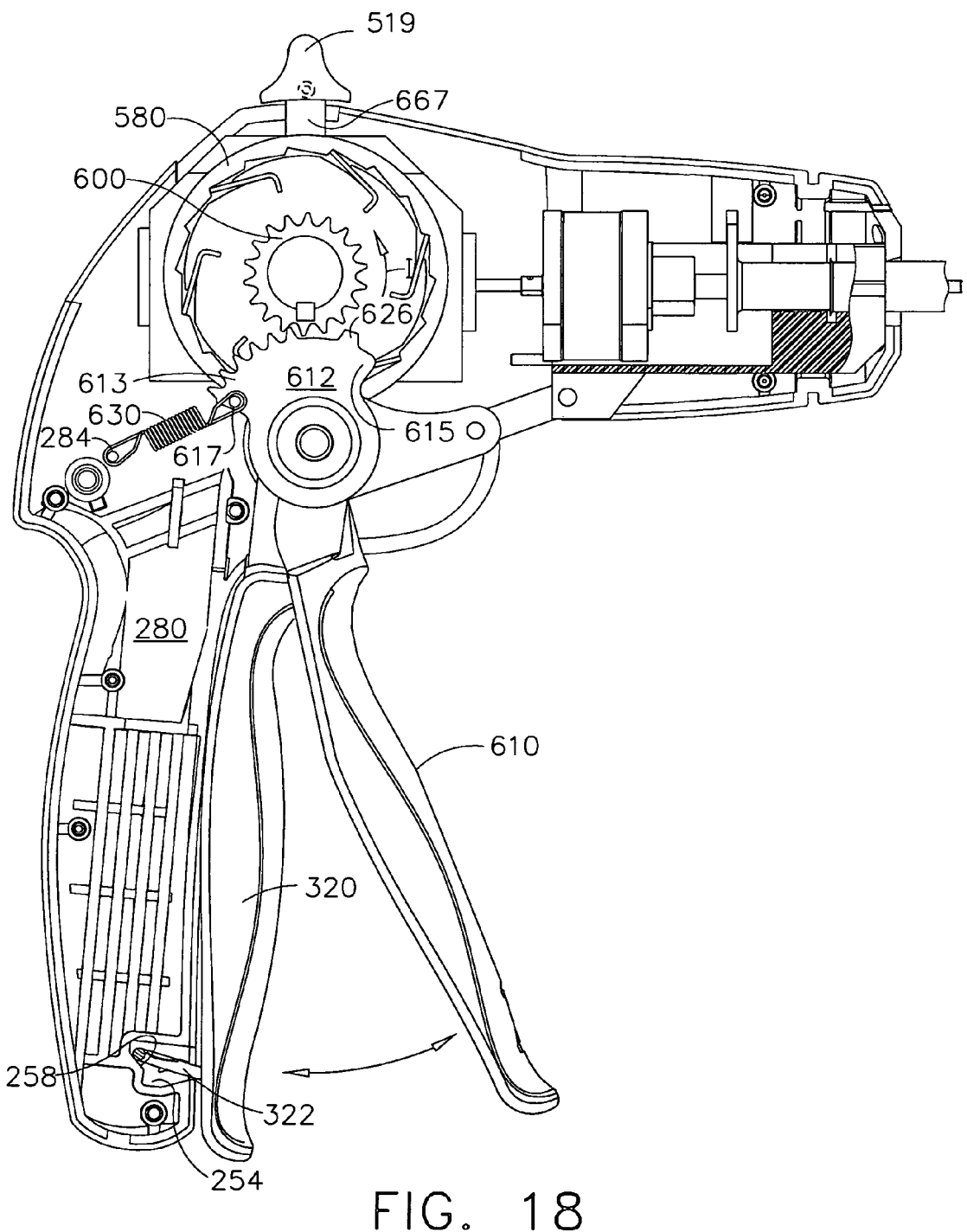
FIG. 18 is another cross-sectional view of a handle assembly of the present invention illustrating movement of the closure trigger to a position wherein it is unlocked from the handle portion.
Figure 19:
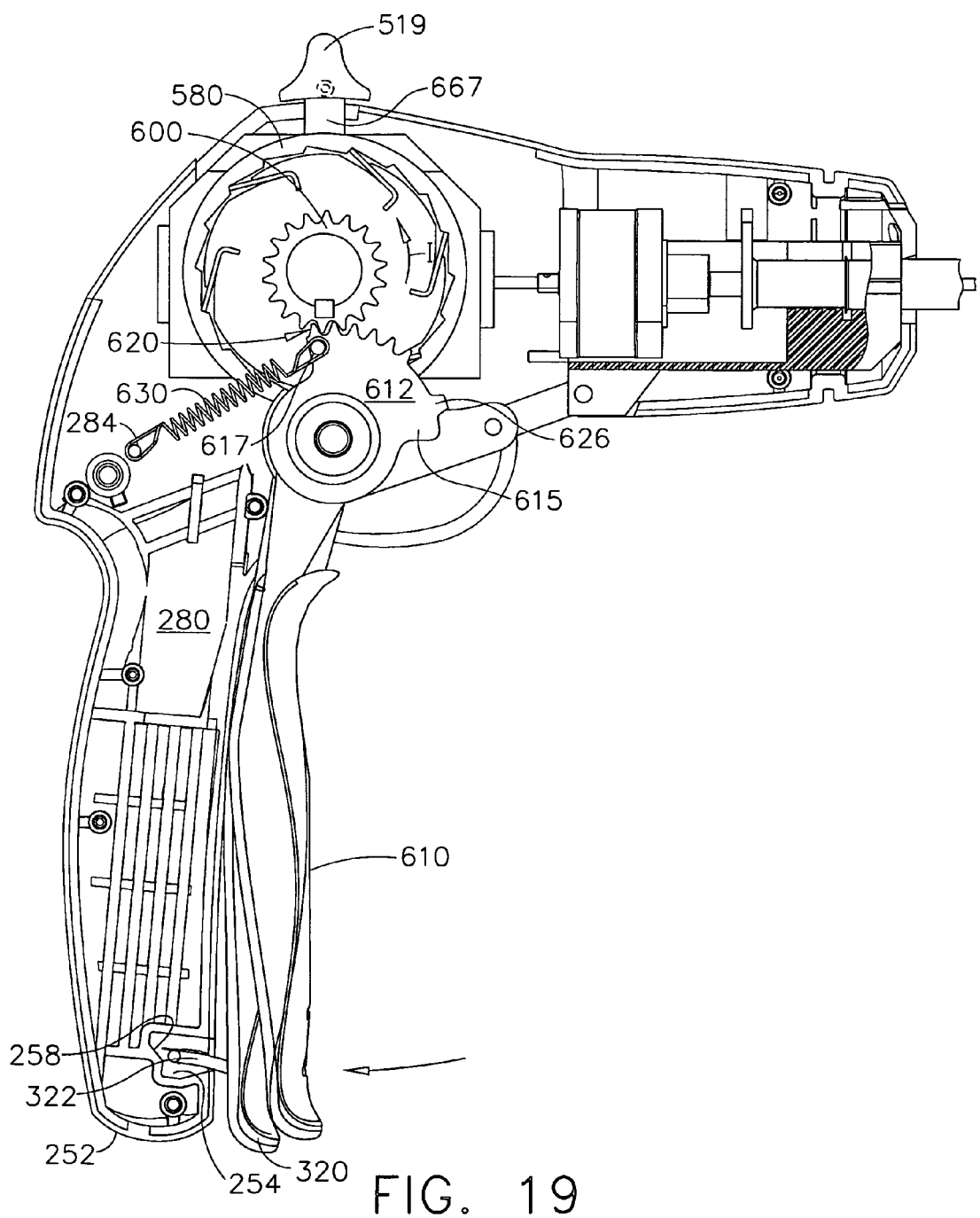
FIG. 19 is another cross-sectional view of a handle assembly of the present invention illustrating the movement of the closure trigger to the fully actuated position.

To release the closure trigger 320 and thereby permit it to be pivoted to the open position, the clinician simply draws the closure trigger 320 further inward toward the pistol grip portion 252 as shown in FIG. 18. As the lock member 322 is moved further into the retention pocket 254, the end of the lock member 322 contacts a sloped surface 258 in the rear of the retention pocket 254 which causes the lock member 322 to flex a sufficient amount to permit it to release from the retention pocket 254 thereby permitting the closure trigger 320 to move away from the pistol grip 252 (FIG. 16). Other releasable locking arrangements could also be employed.

As indicated above, the advancement and retraction of the knife bar 30 is controlled by the firing rod 210 and rotary driven firing screw 240. The firing screw 240 has a splined proximal end 242 that is configured to be coupled to a planetary gear assembly 400 that is supported in the proximal cradle portion 314 of the closure shuttle 300. One embodiment of a planetary gear assembly 400 is depicted in FIGS. 13 and 14. As can be seen in those Figures, the planetary gear assembly 400 includes a planetary case 410 that has a ring gear 412 formed therein. The planetary case 410 supports a first stage gear assembly 420 that has a 3:1 ratio and a second stage gear assembly that has a 3:1 ratio.

The first stage gear assembly 420 includes a first sun gear 422 that is keyed onto an input shaft 414 with a key 416. The input shaft 414 protrudes through a coverplate 418 that mates with the planetary gear case 410 and serves to seal the first stage gear assembly 420 and second stage gear assembly 440 therein. In various embodiments, the first stage gear assembly 420 comprises three first planetary gears 424, 426, 428 that are journaled on corresponding planetary spindles 425, 427, 429, respectively that are attached to a first planetary plate 430. The first planetary gears 424, 426, 428 are in meshing engagement with the first sun gear 422 and the ring gear 412 in the planetary gear case 410. As can be seen in FIG. 13, a first output shaft 432 is attached to the first planetary plate 430 with a key 434.

The second stage gear assembly 440 includes a second sun gear 442 that is also keyed to the first output shaft 432 by key 434. Three second planetary gears 444, 446, 448 are in meshing engagement with the second sun gear 442 and the ring gear 412. The second planetary gears 444, 446, 448 are journaled on three corresponding second planetary spindles 445, 447, 449 that are attached to a second planetary plate 450. A second output shaft 460 is keyed to the second planetary plate 450 by key 462. The second output shaft 460 has an elongate shaft portion 464 that extends through a thrust bearing assembly 470. As can be seen in FIG. 13, the thrust bearing assembly 470 includes a bearing cage 472 that support a plurality of bearings 474. The bearing cage 472 and bearings 474 are located between first and second thrust washers 476 and 478. The elongate shaft portion 464 protrudes through a distal end of the planetary case 410 and is attached to a shaft coupler 480 with a pin or a set screw 482. The shaft coupler 480 is internally splined and adapted to receive therein a splined proximal end 242 of the firing screw 240.

As was indicated above, the movement of the knife bar 30 in the distal direction ("B") is ultimately controlled by the rotation of the firing screw 240 which drives the firing rod 210 and ultimately the knife bar 30. Thus, by rotating the firing screw 240 in the clockwise direction (arrow "D" in FIG. 13) the firing bar 210 is advanced distally ("B"). The rotation of the firing screw 240 is ultimately controlled by a unique and novel shifter assembly 500. As will be discussed in further detail below, the shifter assembly 500 transmits rotational power to the planetary gear set 400 and ultimately to the firing screw 240.

Figure 15:
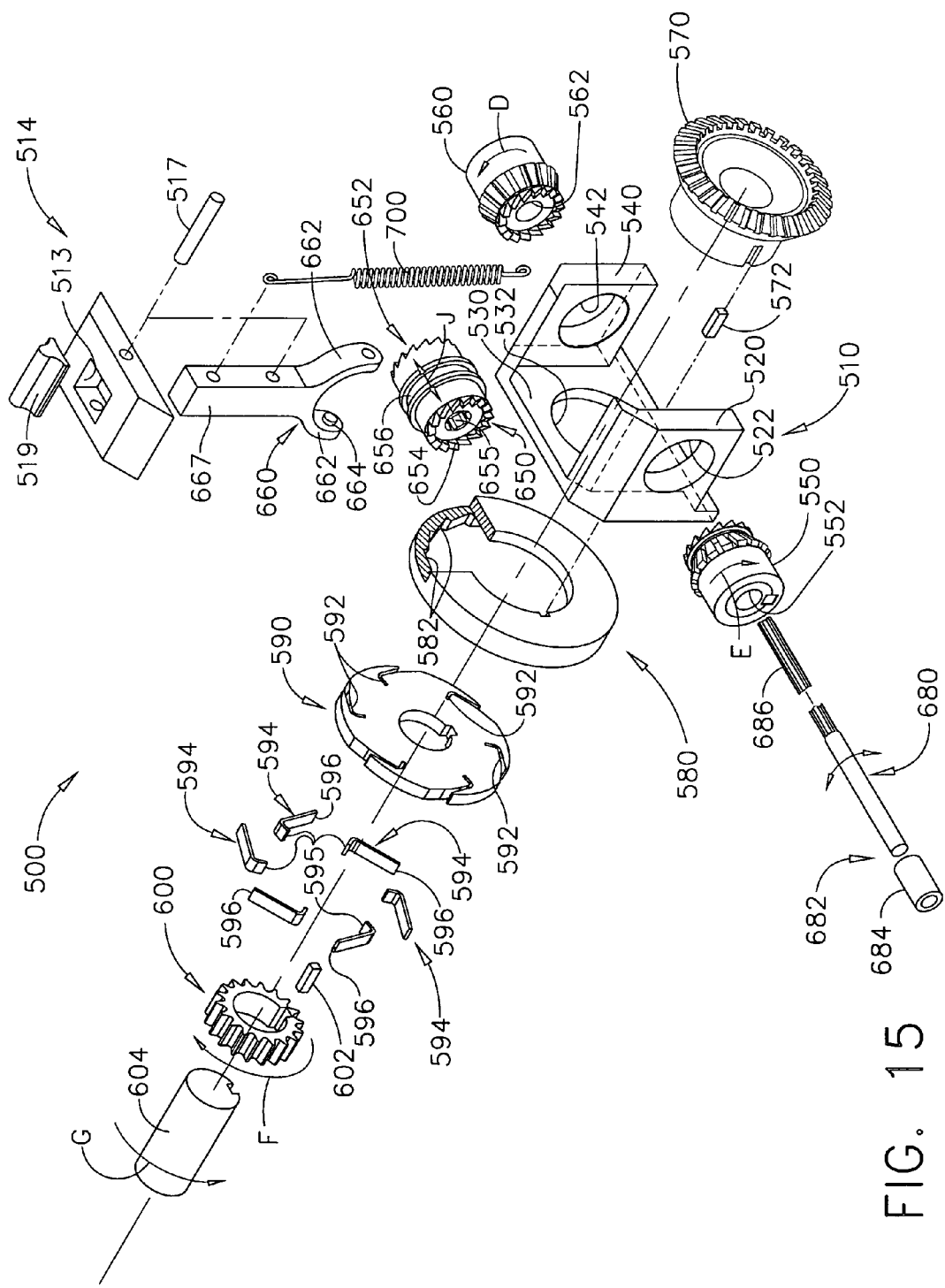
FIG. 15 is an isometric exploded assembly view of a shifter assembly embodiment of the present invention.

In various embodiments, the shifter assembly 500 includes a shifter case 510 that is supported in the housing 250. As can be seen in FIG. 15, the shifter case 510 includes a left hand support arm 520 and a right hand support arm 540 that are separated by a central support member 530. A left hand pinion gear 550 is rotatably supported in a hole 522 in the left hand support arm 520. A right hand pinion gear 560 is similarly rotatably supported within a hole 542 in the right hand support arm 540. A central bevel gear 570 is rotatably supported in a hole 532 in the central support member 530 and is centrally disposed between the right hand pinion gear 560 and left hand pinion gear 550 and is in meshing engagement therewith such that rotation of the central bevel gear causes the right hand pinion gear 560 to rotate in the clockwise "D" direction and the left hand pinion gear 550 to rotate in a counterclockwise "E" direction.

As can be seen in FIG. 15, a ratchet disc 580 is keyed to the central bevel gear 570 with a key 572. Thus, when the ratchet disc 580 is rotated, it causes the central bevel gear 570 to rotate with it. In various embodiments, the shifter assembly 500 further includes a drive disc 590 that has a series of drive springs 594 protruding therefrom around its circumference. The drive springs 594 may be fabricated from spring steel or similar material and each have an attachment stem portion 595 that is inserted into corresponds slots 592 in the drive disc 590. The drive springs 594 may be retained within the corresponding slots 592 by virtue of a friction fit or appropriate adhesive may also be used. The ends 596 of the drive springs 594 protrude out from the drive disc 590 to engage tooth-like ratchet grooves 582 formed into the ratchet disc 580. Thus, when the drive disc 590 is rotated in the direction represented by arrow "F" in FIG. 15, the ends 596 of the drive springs 594 engage the corresponding tooth-like ratchet grooves 582 in the ratchet disc 580 and cause the ratchet disc 580 and central bevel gear 570 to rotate in the "F" direction. However, when the drive disc 590 is rotated in the opposite direction represented by arrow "G" in FIG. 15, the drive springs 594 simply ratchet or slip over the tooth-like ratchet grooves 582 in the ratchet disc 580 and do not transmit rotation to the ratchet disc 580 and central bevel gear 570. In addition, a drive gear 600 is keyed onto a case spindle 604 that is rotatably supported in a spindle socket 266 provided in the right hand case member 260 by a key 602. See FIGS. 10 and 15.

The drive gear 600 is adapted to be drivingly engaged by a firing gear segment 620 formed on an upper end portion 612 of firing trigger 610. More specifically and with reference to FIG. 10, a firing trigger 610 is rotatably supported on a firing post 268 that protrudes from the right hand case member 260 and is received in a corresponding socket (not shown) in the left hand case member 280. The firing post 268 extends through a hole 614 in the upper end of the firing trigger 610 such that the firing trigger 610 can be freely pivoted thereon. The firing trigger 610 may be fabricated from a polymer material and have a segment of gear teeth 620 formed on the upper end 612 of the firing trigger 610 as shown. The gear teeth 622 are adapted to selectively mesh with the teeth 602 of the drive gear 600. As can be seen in FIGS. 16-19 the upper end portion 612 of the firing handle 610 has an arcuate shape. The gear segment 620 is formed on the proximal portion 613 of the upper end portion 612 and a stop member 626 is formed on the distal portion 614 of the upper end portion 612.

FIG. 16 illustrates the firing trigger 610 in the neutral (unfired) position. As can be seen in that Figure, when in that position, the gear teeth 602 of the drive gear 600 that are adjacent the upper end 612 of the firing trigger 610 are not in meshing engagement with the gear segment 620 on the upper end 612 of the firing trigger 610. A firing handle return spring 630 extends between a post 284 on the left hand case member 280 and a post 617 on the upper end 612 of the firing trigger 610. The spring 630 serves to pull the firing trigger 610 into the position shown in FIG. 16. The gear teeth 602 on the drive gear 600 contact the stop member 626 formed on the upper end 612 of the firing trigger 610 to retain the firing trigger 610 in that position and to prevent the firing trigger 610 from rotating in the "G" direction beyond that position. Those of ordinary skill in the art will appreciate that when the clinician draws the firing trigger 610 toward the pistol grip 252 (direction "H"), the gear segment 620 begins to mesh with the gear teeth 602 on the drive gear 600 (FIG. 17) and causes the drive gear 600 to rotate in the direction "I". Once the clinician reaches the end of the stroke, the firing trigger 610 is released and the return spring 630 causes the firing trigger 610 to move to the unfired position depicted in FIG. 16.

The rotational direction of the firing screw 240 is controlled by a shifter gear 650 located in the shifter assembly 500. As can be seen in FIG. 15, the shifter gear 650 is centrally disposed between the right hand bevel gear 560 and the left hand bevel gear 550 and is movable by a shift arm yoke 660 into engagement with those gears 550, 560. More specifically, the shifter gear 650 has a proximal set of gear teeth 652 formed thereon for selective meshing engagement with the right hand pinion gear 560. In addition, the shifter gear 650 has a distal set of gear teeth 654 formed thereon for selective meshing engagement with the left hand pinion gear 550.

In various embodiments, a shifter shaft 680 is coupled to the first input shaft 414 of the planetary gear set 400 and the shifter gear 650. In particular, the shifter shaft 680 has a distal end 682 that is attached to a first coupler 684 by a set screw, adhesive, welding, etc. which is in turn attached to the first input shaft 414 by a set screw, adhesive, welding, etc. The shifter shaft 680 has a splined portion 686 that extends through a hole 552 in the left hand pinion gear 550. The left hand pinion gear 550 does not engage the splined portion 686 of the shifter shaft 680 and can freely rotate in either direction relative thereto. The splined section 686 of the shifter shaft 686 also may extend into a hole 562 in the right hand pinion 560. However, the right hand pinion 560 does not engage the splined section and can freely rotate relative thereto. The splined section 686 of the shifter shaft 680 extends into a splined hole 655 in the shifter gear 650 such that the shifter gear 650 can move axially on the splined section (arrows "J"), but transmits rotation to the shifter shaft 680 by means of the splined interconnection therebetween.

As can be seen in FIG. 15, a yoke groove 656 is formed around the circumference of the shifter gear 650. The yoke 660 includes two opposing yoke arms 662 that each have an inwardly extending pin 664 thereon that is received in the yoke groove 656. Such arrangement permits the shifter gear 650 to rotate relative to the yoke 660. However, the yoke 660 may be used to move the shifter gear 650 axially on the splined section 686 of the shifter shaft 680 between the left hand pinion gear 550 and the right hand pinion gear 560. The shifter assembly 500 has a top member 514 that is attached to the shifter case 510 by adhesive or other suitable fastener means. A shifter arm 667 protrudes from the yoke portion 660 and extends through an opening 513 the top member 514 and is pivotally pinned thereto by a shift arm pin 517. A shifter button 519 is attached to the top end of the shifter arm 667 by adhesive, etc.

In various embodiments, a shifter spring 700 is pinned or otherwise attached to the top of the shifter arm 667 and pinned or other wise attached to the left hand case member 280 such that the shifter spring 700 serves to pull the shifter arm 667 into the position shown in FIG. 12 to thereby cause the proximal gear teeth 652 on the shifter gear 650 to mesh with the gear teeth 564 on the right hand pinion gear 560. When in that position, the clinician can trigger the knife bar 30 by ratcheting the firing trigger 610 as will be discussed below.

In use, the surgical stapling and severing instrument 10 is used as depicted in FIGS. 1, 11, 12 and 16-19. In FIGS. 11 and 16, the instrument 10 is in its start position, having had an unfired, fully loaded staple cartridge 50 snap-fitted into the distal end of the elongate channel 20. Both triggers 320, 610 are forward and the end effector 12 is open, such as would be typical after inserting the end effector 12 through a trocar or other opening into a body cavity. The instrument 10 is then manipulated by the clinician such that tissue to be stapled and severed is positioned between the staple cartridge 50 and the anvil 40.

Figure 17:
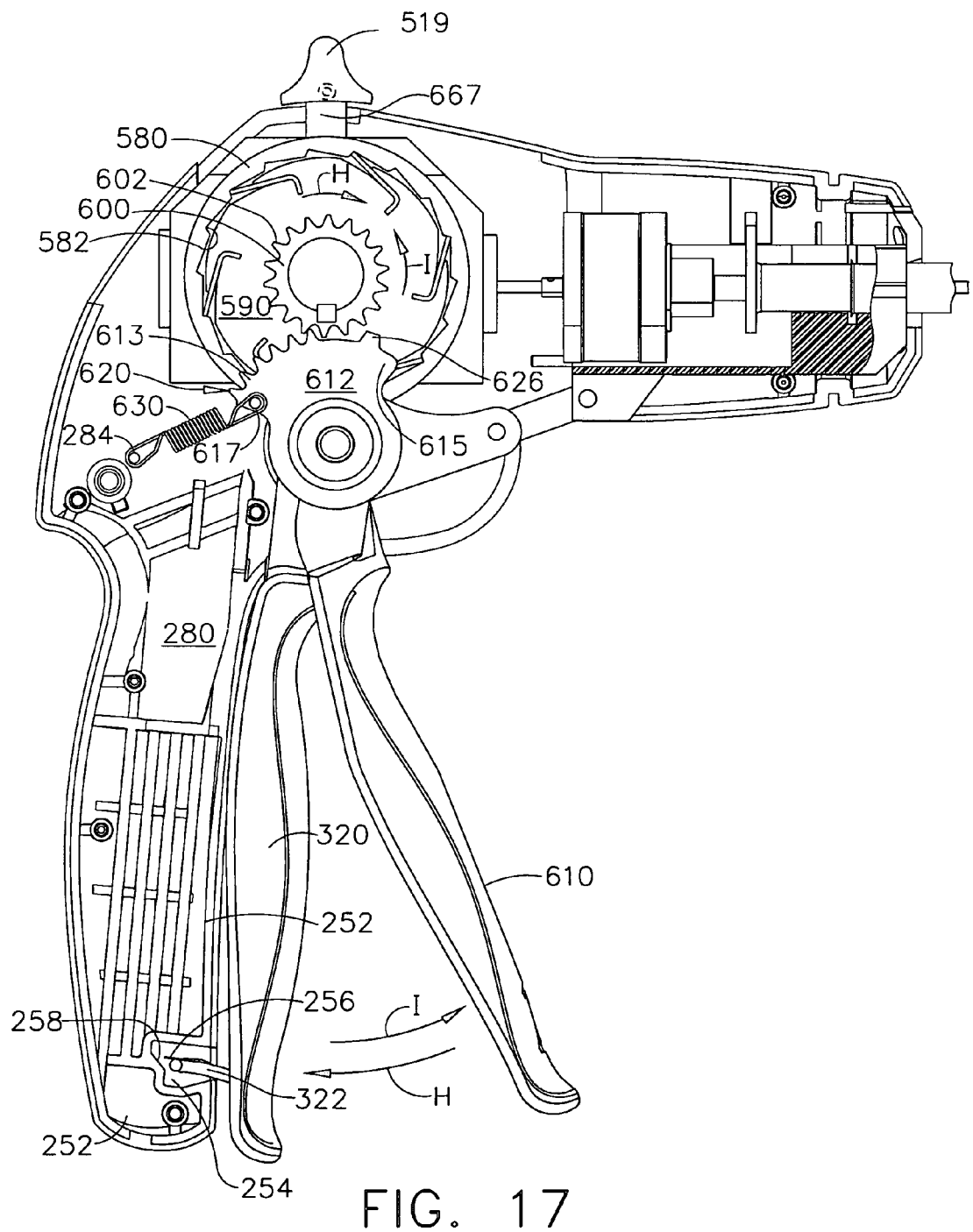
FIG. 17 is another cross-sectional view of a handle assembly embodiment of the present invention with the closure trigger locked in the closed or clamped position resulting in the anvil being locked in the clamped or closed position.

With reference to FIGS. 12 and 17, next, the clinician moves the closure trigger 320 proximally until positioned directly adjacent to the pistol grip 252 such that the retention member 256 frictionally engages the retention pocket 252 in the housing 250 locking the closure trigger 320 in the closed and clamped position. When in that position, the closure linkage 330 also serves to retain the closure trigger 320 in that position as shown in FIG. 12. The retracted knife bar 30 in the end effector 12 does not impede the selective opening and closing of the end effector 12, but rather resides within the anvil pocket 42. With the anvil 40 closed and clamped, the E-beam knife bar 30 is aligned for firing through the end effector 12. In particular, the upper pin 32 is aligned with the anvil slot 44 and the elongate channel 20 is affirmatively engaged about the channel slot 21 by the middle pin 36 and the firing bar cap 34.

With reference to FIGS. 16-19, after tissue clamping has occurred, the clinician moves the firing trigger 610 proximally towards the pistol grip portion 252. Such action cases the gear segment 620 on the upper end 612 of the firing trigger to engage and rotate the drive gear 600 in the "I" direction. Rotation of the drive gear 600 in the "I" direction causes the drive disc 590 to also rotate in that direction. As the drive disc 590 rotates in that direction, the drive springs 594 engage the ratchet teeth 582 on the ratchet disk 580 and cause the ratchet disc 580 to also rotate in the "I" direction. The central bevel gear 570 also rotates with the ratchet disc 580 because it is keyed thereto. As the central bevel gear 570 rotates, it also causes the left hand pinion gear 550 to rotate in the "E" direction and the right hand pinion gear 560 to rotate in the "D" direction. See FIG. 15.

When the shifter gear 650 is brought into meshing engagement with the right hand pinion gear 560 as shown in FIGS. 11 and 12, movement of the central bevel gear 570 causes the right hand pinion gear 560 and shifter gear 650 to rotate in the "D" direction. Because of the splined connection between the shifter shaft 680 and the shifter gear 650, the shifter shaft 680 is also caused to rotate in the "D" direction. Such rotary drive motion is transferred to the firing screw 240 through the planetary gear assembly 400. As the firing screw 240 rotates in the "D" direction, the firing bar 210 is driven distally which causes the connection block 160 and knife bar 30 to move proximally. The clinician continues to ratchet the firing trigger 610 until the knife bar 30 is returned to the unfired position.

When the clinician has moved the firing trigger 610 to the proximal position adjacent the closure trigger 320, the clinician can release the firing trigger 610 and the return spring 630 will return the firing trigger 610 to the unfired position (FIG. 16). As the firing trigger 610 is returned to the unfired position, the gear segment 620 thereon will impart a rotation in the "H" direction to the drive gear 600. The drive gear 600 also causes the drive disc 590 to rotate in the direction "H". However, the drive springs 594 ratchet over the ratchet teeth 582 in the ratchet disc 580 and thus the rotational motion is not transmitted thereto. The clinician continues to ratchet the firing trigger 610 until the knife bar 30 can no longer be advanced distally through the cartridge 50.

The clinician can then return the knife bar 30 to the unfired position, by moving the shifter button 519 in the distal direction to cause the shifter gear 650 to disengage the right hand pinion gear 560 and mesh with the left hand pinion gear 550. Thereafter, the clinician simply ratchets the firing trigger 610 in the same manner which causes the left hand pinion gear 550 to rotate in the "E" direction. Such rotational motion is transmitted to the shifter shaft 680 and to the firing screw 240 through the planetary gear assembly 400. As the firing screw 240 rotates in the "E" direction, the nuts 247 draw the firing bar 210 proximally. The firing bar 210 then draws the connector block 160 and knife bar 30 proximally until the knife bar 30 reaches the unfired position wherein the spent cartridge 50 may be removed from the elongate channel 20 and replaced with a new unfired cartridge or, in the alternative the entire unit 10 may be properly discarded.

As can be appreciated from the above-described firing and retraction sequences, the firing and retraction actions are accomplished through multiple actuations of the firing trigger. For example, in one embodiment, the clinician must actuate (i.e., move the firing handle from its unfired position (FIG. 16) to its fired position (FIG. 19)) six times to completely fire all of the staples in a conventional 60 mm end effector. Likewise, to completely retract the knife bar 30 to the unfired position wherein the staple cartridge 50 may be removed from the elongate channel 20, the clinician would have to move the shifter button 519 to the retraction position and actuate the firing trigger an equal number of times—in this example six times. However, the unique and novel attributes and advantages of the present invention may be employed in connection with a host of different sizes of end effectors. Thus, when shorter end effectors are employed, less actuations of the firing trigger may be required to completely fire the staples and thereafter return the knife bar to a fully retracted position. For example, it is within the scope of this invention to be employed with end effectors that would require only one or more than one actuations of the firing trigger to fire the staples and only one or more than one actuations to move the firing and cutting device to a fully retracted position.

As indicated above, the distal spine section 110 is attached to the proximal spine section 130 such that it can freely rotate relative thereto. Likewise, the closure tube assembly 170 can freely rotate on the spine assembly 100. To facilitate rotation of the end effector 12 relative to the handle assembly 200, the handle assembly 200 is provided with a rotation grip assembly 710 that can be rotated relative to the handle assembly 200 and cause rotation of the end effector 12. More specifically and with reference to FIGS. 1 and 10, the grip assembly 710 comprises a right hand grip segment 720 and a left hand grip segment 730 (shown in FIG. 1) that are adapted to mate with each other and rotate around the distal end 251 of the housing 250. The right hand grip segment 720 and left hand grip segment 730 may be fabricated from polymers or other suitable materials and attached to each other by snap features, adhesive, screws, etc. Each segment 720, 730 has an arcuate rail segment 722 formed therein that is adapted to ride in a groove 259 formed in the housing 250 when the right hand case member 260 and left hand case member 280 are attached together. Thus, the rail segments 722 serve to retain the grip assembly 710 on the housing 250 while facilitating its rotation relative thereto. Each grip segment 720, 730 further has a tube rotation segment 724 formed therein that cooperate together to extend into a hole 191 in the proximal closure tube segment 190. Thus, rotation of the grip housing 710 relative to the handle housing 250 causes the closure tube assembly 170 to rotate on the proximal spine segment 130. It will be understood that the distal closure tube segment 180 does not rotate relative to the distal spine section 110, but rather causes the distal spine section 110 to rotate with it relative to the proximal spine section 130. The flange 197 on the proximal end 196 of the proximal closure tube segment is received within a corresponding groove in the grip assembly 710. Such arrangement permits the clinician to easily rotate the end effector 12 relative to the handle assembly 200 after the end effector 12 has been inserted through the trocar into the patient.

While the present invention has been illustrated by description of several embodiments and while the illustrative embodiments have been described in considerable detail, it is not the intention of the applicant to restrict or in any way limit the scope of the appended claims to such detail. Additional advantages and modifications may readily appear to those skilled in the art.

For example, by manufacturing the elongate channel utilizing convention dies stamping techniques may lead to reduced manufacturing costs for that component. Likewise by stamping the anvil from metal utilizing conventional stamping techniques can also reduce the manufacturing costs commonly encountered when manufacturing such components. In addition, the unique and novel ratchet drive arrangement for firing the device eliminates the need the for battery or pneumatically powered components which can increase the overall cost of the device.

The devices disclosed herein can be designed to be disposed of after a single use, or they can be designed to be used multiple times. In either case, however, the device can be reconditioned for reuse after at least one use. Reconditioning can include an combination of the steps of disassembly of the device, followed by cleaning or replacement of particular pieces, and subsequent reassembly. In particular, the device can be disassembled, and any number of particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Those of ordinary skill in the art will appreciate that the reconditioning of a device can utilize a variety of different techniques for disassembly, cleaning/replacement, and reassembly. Use of such techniques, and the resulting reconditioned device, are all within the scope of the present application.

Preferably, the invention described herein will be processed before surgery. First a new or used instrument is obtained and, if necessary, cleaned. The instrument can then be sterilized. In one sterilization technique, the instrument is placed in a closed and sealed container, such as a plastic or TYVEK® bag. The container and instrument are then placed in a field of radiation that can penetrate the container, such as gamma radiation, x-rays, or higher energy electrons. The radiation kills bacteria on the instrument and in the container. The sterilized instrument can then be stored in the sterile container. The sealed container keeps the instrument sterile until it is opened in the medical facility.

Any patent, publication, or information, in whole or in part, that is said to be incorporated by reference herein is incorporated herein only to the extent that the incorporated material does not conflict with existing definitions, statements, or other disclosure material set forth in this document. As such the disclosure as explicitly set forth herein supersedes any conflicting material incorporated herein by reference.

The invention which is intended to be protected is not to be construed as limited to the particular embodiments disclosed. The embodiments are therefore to be regarded as illustrative rather than restrictive. Variations and changes may be made by others without departing from the spirit of the present invention. Accordingly, it is expressly intended that all such equivalents, variations and changes which fall within the spirit and scope of the present invention as defined in the claims be embraced thereby.

What is claimed is:

1. A surgical instrument comprising:
   a handle assembly;
   a closure drive supported by said handle assembly and configured to generate a closing motion and an opening motion;
   a firing drive supported by said handle assembly and configured to selectively generate a rotary firing motion upon actuation of a firing trigger operably coupled to said handle assembly and a rotary retraction motion upon another actuation of the firing trigger;
   an elongate shaft assembly coupled to said handle assembly and communicating with said closure drive and said firing drive to separately transfer said closing and opening motions and said rotary firing motion; and
   an end effector coupled to said elongate shaft assembly, said end effector comprising:
      an elongate channel sized to receive a staple cartridge therein;
      an anvil pivotally coupled to said elongate channel and being pivotally
      responsive to said open and closing motions from said elongate shaft assembly; and
      a cutting and severing member operably supported within said elongate
      channel and being responsive to said rotary firing and retraction motions from said elongate shaft assembly.

2. The surgical instrument of claim 1 wherein said elongate channel is metal and formed by stamping.

3. The surgical instrument of claim 1 wherein said anvil is metal and formed by stamping.

4. The surgical instrument of claim 1 wherein said elongate shaft assembly comprises:
   a spine assembly attached to said closure drive and said elongate channel; and
   a closure tube assembly coupled to said handle assembly and extending over said spine assembly, said spine assembly axially movable relative to said closure tube assembly in response to said closing and opening motions generated by said closure drive, said closure tube assembly configured to actuate said anvil between open and closed positions in response to said axial movement of said spine assembly within said closure tube assembly.

5. The surgical instrument of claim 4 wherein said spine assembly comprises:
   a proximal spine section coupled to said handle assembly; and
   a distal spine section coupled to said proximal spine section and being rotatable relative thereto.

6. The surgical instrument of claim 5 wherein said closure tube assembly is selectively rotatable relative to said handle assembly.

7. The surgical instrument of claim 4 wherein said closure drive comprises:
   a closure shuttle movably supported by said handle assembly, said closure shuttle supporting a proximal end of said spine assembly therein; and
   a closure trigger operably affixed to said handle assembly and said closure shuttle, said closure trigger operable to apply closing and opening forces to said closure shuttle.

8. The surgical instrument of claim 1 wherein said firing drive comprises:
   a firing rod supported within said elongate shaft assembly for selective axial travel therein, said firing rod communicating with said cutting and severing member such that upon an application of the rotary firing motion thereto, said firing rod causes said cutting and severing member to move in a distal direction through said elongate channel and upon application of the rotary retraction force to said firing rod, said firing rod causes said cutting and severing member to move in a proximal direction; and
   a shifter assembly supported within said handle assembly and being selectively movable between a firing orientation for generating said rotary firing motion and a retraction orientation for generating said rotary retraction motion; said shifter assembly communicating with said firing rod such that when said firing trigger is actuated when said shifter assembly is in firing orientation, said shifter assembly applies said rotary firing motion to said firing rod and when said firing trigger is actuated when said shifter assembly is in said retraction orientation, said shifter assembly applies said rotary retraction motion to said firing rod.

9. The surgical instrument of claim 8 further comprising a shifter button supported by said handle assembly for selectively moving said shifter assembly between said firing orientation and said retraction orientation.

10. The surgical instrument of claim 8 wherein said shifter assembly comprises:
    a first pinion gear operably supported within said handle assembly;
    a second pinion gear operably supported within said handle assembly;
    a central bevel gear in meshing engagement with said first and second pinion gears;
    a ratchet assembly coupled to said central bevel gear and said firing trigger such that actuation of said firing trigger causes said ratchet assembly to rotate said central bevel gear in a first direction; and
    a shifter gear centrally disposed between said first and second pinion gears and being selectively movable between a position wherein said shifter gear meshes with said first gear and transmits said rotary firing motion to said firing rod and another position wherein said shifter gear meshes with said second gear and transmits said rotary retraction motion to said firing rod.

11. The surgical instrument of claim 10 further comprising:
a shifter shaft coupled to said shifter gear;
a gear assembly coupled to said shifter shaft; and
a firing screw coupled to said gear assembly and said firing rod such that rotation of said firing screw in one direction causes said firing rod to move distally and rotation of said firing screw in an opposite direction causes said firing rod to move in a proximal direction.

12. A method for processing an instrument for surgery, said method comprising:
obtaining said surgical instrument of claim 1;
sterilizing said surgical instrument; and
storing said instrument in a sterile container.

13. A cutting and fastening instrument, comprising:
a handle assembly;
a closure shuttle movably supported by said handle assembly;
a closure trigger operably supported by said handle assembly and operable to apply a closing and opening force to said closure shuttle;
an elongate spine assembly having a distal end and a proximal end, said proximal end supported by said closure shuttle and said distal end coupled to an elongate channel configured to receive a staple cartridge therein;
an anvil pivotally coupled to said elongate channel;
a closure tube assembly supported on said elongate spine assembly and coupled to said handle assembly, said closure tube assembly cooperating with said anvil such that upon application of said closure force to said closure shuttle, said spine assembly moves distally within said closure tube assembly causing said anvil to pivot to a closed position and upon application of said opening force to said closure shuttle, said spine assembly moves proximally within said closure tube assembly causing said anvil to pivot to an open position;
a cutting and severing member operably supported within said elongate channel;
a shifter assembly supported in said handle assembly and being selectively movable between a firing orientation and a retraction orientation, said shifter assembly cooperating with a firing trigger such that upon actuation of said firing trigger when said shifter assembly is in said firing orientation, said shifter assembly applies a rotary firing motion to said cutting and severing member to drive said cutting and severing member distally through said elongate channel and such that upon another actuation of said firing trigger when said shifter assembly is in said retraction orientation, said shifter assembly applies a rotary retraction motion to said cutting and severing member to drive said cutting and severing member proximally through said elongate channel.

14. The surgical instrument of claim 13 wherein said elongate channel is metal and formed by stamping.

15. The surgical instrument of claim 13 wherein said anvil is metal and formed by stamping.

16. The surgical instrument of claim 13 wherein said elongate spine assembly is selectively rotatable relative to said handle assembly.

17. The surgical instrument of claim 13 further comprising means for releasably retaining the closure trigger in a locked position.

18. The surgical instrument of claim 13 further comprising:
a firing rod supported within a portion of said elongate spine assembly for selective axial travel therein, said firing rod communicating with said shifter assembly and said cutting and severing member such that upon an application of the rotary firing motion to said firing rod, said firing rod causes said cutting and severing member to move in a distal direction through said elongate channel and upon application of the rotary retraction motion to said firing rod by said shifter assembly, said firing rod causes said cutting and severing member to move in a proximal direction.

19. The surgical instrument of claim 13 further comprising a shifter button supported by said handle assembly for selectively moving said shifter assembly between said firing orientation and said retraction orientation.

20. A surgical instrument comprising:
a handle assembly;
closure means supported by said handle assembly for generating a closing motion and an opening motion;
firing means supported by said handle assembly for manually generating a rotary firing motion and a rotary retraction motion upon manual actuation of a firing trigger operably coupled to said handle assembly;
cartridge support means coupled to said handle assembly for supporting a staple cartridge therein;
cutting means supported within said cartridge support means;
force transmitting means coupled to said handle assembly and communicating with said closure means and said firing means to separately transfer said closing motion, said firing motion and said retraction motion to said cutting means; and
anvil means pivotally coupled to said cartridge support means, said anvil means being pivotally responsive to said open and closing motions from said force transmitting means.

21. A surgical instrument, comprising:
an end effector, comprising:
a channel configured to receive a staple cartridge; and
a cutting member operably supported within said channel;
a firing member operably engaged with said cutting member;
a trigger;
a firing drive configured to advance said firing member toward said end effector and to move said cutting member relative to said channel, wherein said trigger is selectively engageable with said firing drive to operate said firing drive; and
a reversing drive configured to retract said firing member away from said end effector and to move said cutting member relative to said channel, wherein said trigger is selectively engageable with said reversing drive to operate said reversing drive, and wherein said trigger can be operably disengaged from said firing drive and operably engaged with said reversing drive prior to or upon an actuation of said trigger.

22. A surgical instrument, comprising:
an end effector;
a firing member;
a trigger;
a firing drive selectively engageable with said firing member, wherein said firing drive is configured to advance said firing member relative to said end effector upon an actuation of said trigger; and
a reversing drive selectively engageable with said firing member, wherein said reversing drive includes a gear configured to retract said firing member relative to said end effector upon a subsequent actuation of said trigger.

23. A surgical instrument, comprising:
an end effector;
a firing member;
a trigger;
a firing drive selectively engageable with said firing member, wherein said firing drive is configured to advance said firing member relative to said end effector upon an actuation of said trigger; and
a gear train, comprising:
a first gear operably engaged with said firing member;
a second gear operably engaged with said trigger, wherein said second gear is selectively operable with said first gear such that a subsequent actuation of said trigger retracts said firing drive relative to said end effector.

\* \* \* \* \*